United States Patent
Seymour et al.

(10) Patent No.: US 9,643,027 B2
(45) Date of Patent: May 9, 2017

(54) WAVEGUIDE NEURAL INTERFACE DEVICE

(71) Applicant: NeuroNexus Technologies, Inc., Ann Arbor, MI (US)

(72) Inventors: John P. Seymour, Ann Arbor, MI (US); Mayurachat Ning Gulari, Ann Arbor, MI (US); Daryl R. Kipke, Dexter, MI (US); Kc Kong, Ann Arbor, MI (US)

(73) Assignee: NEURONEXUS TECHNOLOGIES, INC., Ann Arbor, MI (US)

( * ) Notice: Subject to any disclaimer, the term of this patent is extended or adjusted under 35 U.S.C. 154(b) by 28 days.

(21) Appl. No.: 14/521,552

(22) Filed: Oct. 23, 2014

(65) Prior Publication Data

US 2015/0047179 A1 Feb. 19, 2015

Related U.S. Application Data

(63) Continuation of application No. 12/940,748, filed on Nov. 5, 2010, now Pat. No. 8,870,857.

(Continued)

(51) Int. Cl.
*A61N 5/06* (2006.01)
*A61B 5/00* (2006.01)
*A61B 5/04* (2006.01)

(52) U.S. Cl.
CPC .......... *A61N 5/0622* (2013.01); *A61B 5/0084* (2013.01); *A61B 5/04001* (2013.01);
(Continued)

(58) Field of Classification Search
None
See application file for complete search history.

(56) References Cited

U.S. PATENT DOCUMENTS 3,921,916 A 11/1975 Bassous
4,461,304 A 7/1984 Kuperstein
(Continued)

FOREIGN PATENT DOCUMENTS

WO 0112115 2/2001
WO 0236002 5/2002
(Continued)

OTHER PUBLICATIONS

Kaplan, et al., "A Novel Fabrication Method of Capillary Tubes on Quartz for Chemical Analysis Application", Industrial Microelectronics Center, PO Box 1084, S-164 21 Kista, Sweden, Fax +46 87505430, 1994.
(Continued)

*Primary Examiner* — Erica Lee
(74) *Attorney, Agent, or Firm* — Haynes and Boone, LLP; Taylor Merritt Meacham

(57) ABSTRACT

A waveguide neural interface device including: a neural device implantable in tissue and including an array of electrode sites that electrically communicate with their surroundings, in which the array of electrode sites includes at least one recording electrode site; and a waveguide, coupled to the neural device, that carries light along a longitudinal axis and includes a light directing element that redirects the carried light from the waveguide to illuminate selectively targeted tissue, in which at least a portion of the redirected light is directed laterally away from the longitudinal axis and the recording electrode site is configured to sample illuminated tissue. A method for assembling a waveguide neural interface device is also described.

34 Claims, 15 Drawing Sheets

Related U.S. Application Data

(60) Provisional application No. 61/258,494, filed on Nov. 5, 2009, provisional application No. 61/321,089, filed on Apr. 5, 2010.

(52) U.S. Cl.
CPC .... *A61B 5/4076* (2013.01); *A61B 2562/0233* (2013.01); *A61B 2562/046* (2013.01); *A61N 2005/0626* (2013.01); *A61N 2005/0643* (2013.01); *Y10T 29/49016* (2015.01)

(56) References Cited

U.S. PATENT DOCUMENTS

| | | | |
|---|---|---|---|
| 4,660,925 | A | 4/1987 | McCaughan |
| 4,904,237 | A | 2/1990 | Janese |
| 4,986,628 | A | 1/1991 | Lozhenko et al. |
| 5,042,980 | A | 8/1991 | Baker et al. |
| 5,196,005 | A | 3/1993 | Doiron et al. |
| 5,207,709 | A | 5/1993 | Picha |
| 5,269,777 | A | 12/1993 | Doiron et al. |
| 5,308,442 | A | 5/1994 | Taub et al. |
| 5,325,451 | A | 6/1994 | Hartman et al. |
| 5,385,635 | A | 1/1995 | O'Neill |
| 5,546,494 | A | 8/1996 | Eda |
| 5,548,670 | A | 8/1996 | Koike |
| 5,580,932 | A | 12/1996 | Koike |
| 5,585,827 | A | 12/1996 | Murakami |
| 5,588,597 | A | 12/1996 | Reinecke et al. |
| 5,721,795 | A | 2/1998 | Pelka |
| 5,938,694 | A | 8/1999 | Jaraczewski et al. |
| 5,946,441 | A | 8/1999 | Esch |
| 6,071,302 | A | 6/2000 | Sinofsky et al. |
| 6,205,361 | B1 | 3/2001 | Kuzma et al. |
| 6,228,111 | B1 | 5/2001 | Törmäläet al. |
| 6,374,143 | B1 | 4/2002 | Berrang et al. |
| 6,559,636 | B1 | 5/2003 | Brunsch et al. |
| 6,593,130 | B1 | 7/2003 | Sen et al. |
| 6,834,200 | B2 | 12/2004 | Moxon et al. |
| 6,878,643 | B2 | 4/2005 | Krulevitch et al. |
| 6,921,413 | B2 | 7/2005 | Mahadevan-Jansen et al. |
| 7,010,356 | B2 | 3/2006 | Jog et al. |
| 7,011,680 | B2 | 3/2006 | Alt |
| 7,076,143 | B2 | 7/2006 | Takahashi |
| 7,194,158 | B2 | 3/2007 | Schultheis et al. |
| 7,260,289 | B1 | 8/2007 | Gunn et al. |
| 7,547,551 | B2 | 6/2009 | Schuler et al. |
| 7,670,838 | B2 | 3/2010 | Deisseroth et al. |
| 7,736,382 | B2 | 6/2010 | Webb et al. |
| 7,781,195 | B1 | 8/2010 | Heller et al. |
| 7,937,143 | B2 | 5/2011 | Demarais et al. |
| 2002/0198446 | A1 | 12/2002 | Hill et al. |
| 2003/0100823 | A1 | 5/2003 | Kipke et al. |
| 2004/0053873 | A1 | 3/2004 | Barman et al. |
| 2004/0106169 | A1 | 6/2004 | Evans |
| 2004/0199235 | A1 | 10/2004 | Younis |
| 2005/0004627 | A1 | 1/2005 | Gibson et al. |
| 2005/0021117 | A1 | 1/2005 | He et al. |
| 2005/0137647 | A1 | 6/2005 | Wallace et al. |
| 2005/0180713 | A1 | 8/2005 | Heideman et al. |
| 2006/0024359 | A1 | 2/2006 | Walker et al. |
| 2006/0129210 | A1 | 6/2006 | Cantin et al. |
| 2006/0192230 | A1 | 8/2006 | Wood et al. |
| 2006/0247749 | A1 | 11/2006 | Colvin |
| 2006/0258951 | A1 | 11/2006 | Bleich et al. |
| 2006/0265014 | A1 | 11/2006 | Demarais et al. |
| 2006/0276866 | A1 | 12/2006 | McCreery |
| 2006/0282014 | A1 | 12/2006 | Kipke et al. |
| 2007/0060984 | A1* | 3/2007 | Webb .................. A61N 5/0601 607/89 |
| 2007/0073130 | A1 | 3/2007 | Finch et al. |
| 2007/0112404 | A1 | 5/2007 | Mann et al. |
| 2007/0123765 | A1 | 5/2007 | Hetke et al. |
| 2007/0135885 | A1 | 6/2007 | Risi |
| 2007/0167903 | A1 | 7/2007 | Sanchez-Ramos et al. |
| 2007/0261127 | A1 | 11/2007 | Boyden et al. |
| 2007/0270675 | A1 | 11/2007 | Kane et al. |
| 2008/0085265 | A1 | 4/2008 | Schneider et al. |
| 2008/0177363 | A1 | 7/2008 | Schouenborg |
| 2008/0208283 | A1 | 8/2008 | Vetter et al. |
| 2008/0227139 | A1 | 9/2008 | Deisseroth et al. |
| 2009/0088680 | A1 | 4/2009 | Aravanis et al. |
| 2009/0118800 | A1 | 5/2009 | Deisseroth et al. |
| 2009/0118806 | A1 | 5/2009 | Vetter et al. |
| 2009/0132042 | A1 | 5/2009 | Hetke et al. |
| 2009/0187196 | A1 | 7/2009 | Vetter |
| 2009/0201698 | A1* | 8/2009 | Klick .................. G02B 6/0018 362/555 |
| 2009/0240314 | A1 | 9/2009 | Kong et al. |
| 2009/0248118 | A1 | 10/2009 | Bradley et al. |
| 2010/0030043 | A1* | 2/2010 | Kuhn .................. A61B 5/0031 600/339 |
| 2010/0030298 | A1 | 2/2010 | Martens et al. |
| 2010/0174329 | A1* | 7/2010 | Dadd et al. ........................ 607/3 |
| 2010/0190229 | A1 | 7/2010 | Zhang et al. |
| 2010/0204638 | A1 | 8/2010 | Hobbs et al. |
| 2010/0240991 | A1 | 9/2010 | Bartlett |
| 2010/0262212 | A1 | 10/2010 | Shoham et al. |
| 2010/0268150 | A1 | 10/2010 | Mohanty et al. |
| 2011/0060377 | A1 | 3/2011 | Howard |
| 2011/0087126 | A1 | 4/2011 | Zorzos et al. |
| 2011/0087311 | A1 | 4/2011 | Zorzos et al. |
| 2011/0105998 | A1 | 5/2011 | Zhang et al. |
| 2011/0112179 | A1 | 5/2011 | Airan et al. |
| 2011/0125077 | A1 | 5/2011 | Denison et al. |
| 2011/0154655 | A1 | 6/2011 | Hetke et al. |

FOREIGN PATENT DOCUMENTS

| | | |
|---|---|---|
| WO | 02096482 | 12/2002 |
| WO | 2005039696 | 5/2005 |
| WO | 2011010257 | 1/2011 |

OTHER PUBLICATIONS

Lin, et al., "Silicon-Processed Microneedles", IEEE Journal of Microelectromehani al Systems vol. 8, No. 1, Mar. 1999.

Seymour, et al., "Neural Probe Design for Reduced Tissue Encapsulation in CNS", Science Direct Biomaterials 28 (2007) 3594-3607 Department of Biomedical Engineering, University of Michigan, 2212 Lurie Biomedical Engineering Building, 1101 Avenue, Ann Arbor, MI 48109-2099, USA, Mar. 27, 2007.

Seymour, et al., "The Insulation Performance of Reactibe Parylene Films in Implantable Electronic Devices", Biomaterials 30 (2006=9) 6158-6167 Contents lists available at Science Direct, 2009.

* cited by examiner

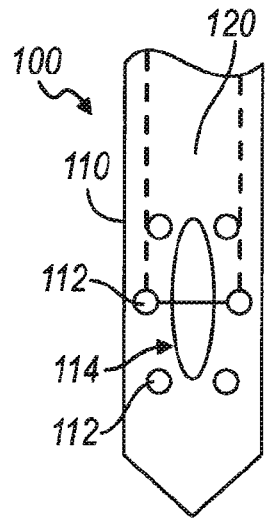
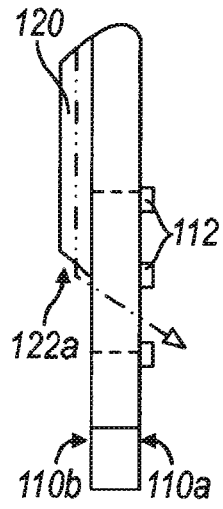
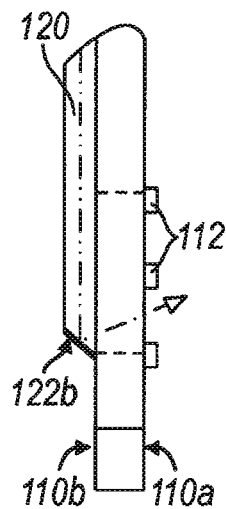
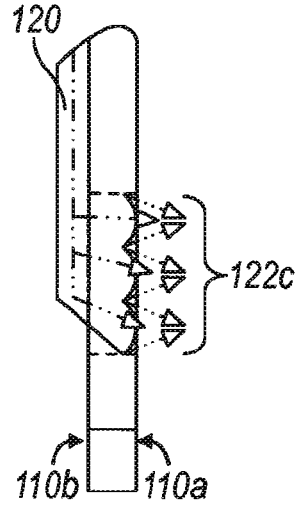
FIG. 1A  FIG. 1B  FIG. 1C  FIG. 1D
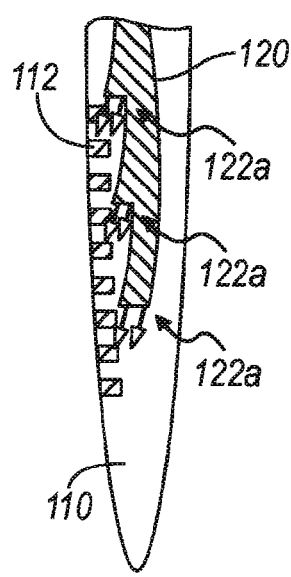
FIG. 2

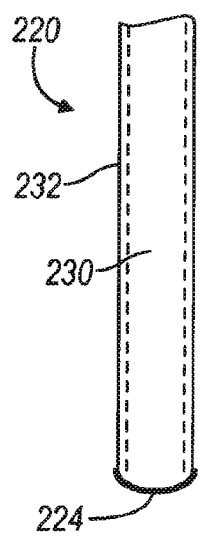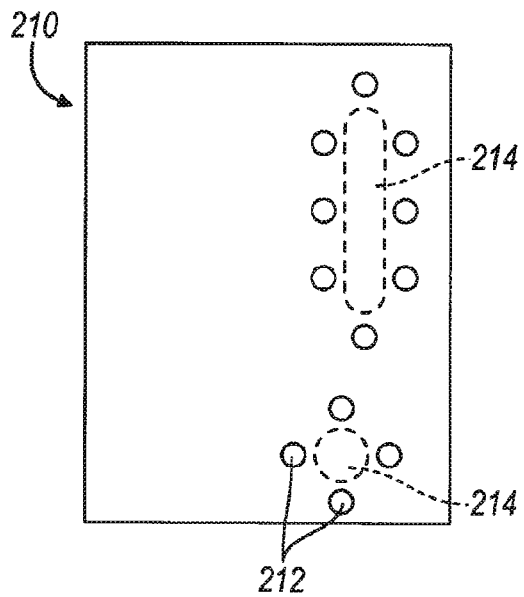
FIG. 14A          FIG. 14B
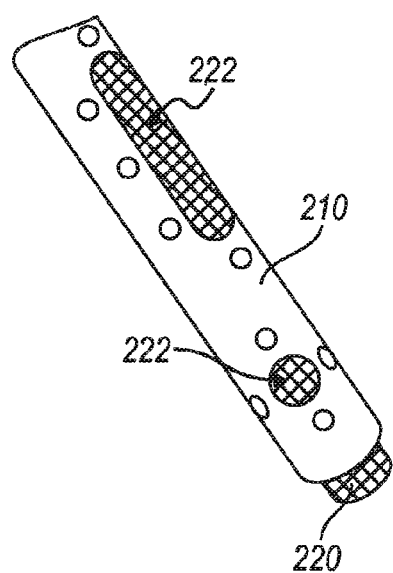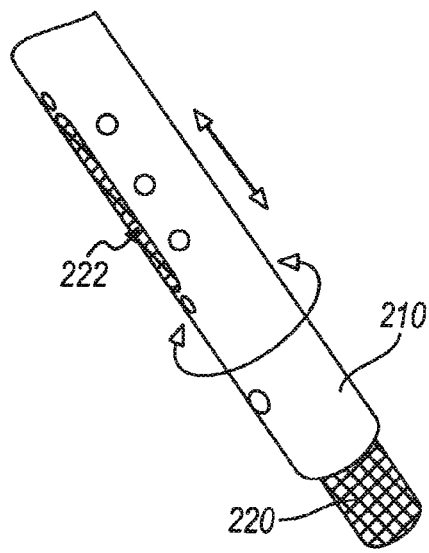
FIG. 14C          FIG. 14D

WAVEGUIDE NEURAL INTERFACE DEVICE

CROSS-REFERENCE TO RELATED APPLICATIONS

This application is a divisional application of U.S. patent application Ser. No. 12/940,748, filed on Nov. 5, 2010, now U.S. Pat. No. 8,870,857, which claims the benefit of U.S. Provisional Applications No. 61/258,494 filed 5 Nov. 2009 and 61/321,089 filed 5 Apr. 2010, which are both incorporated in their entirety by this reference.

TECHNICAL FIELD

This invention relates generally to the neural device field, and more specifically to an improved waveguide neural interface device in the neural device field.

BACKGROUND

Advances in neuroscience have largely depended on the advance of technology, which continually provides new methods to perturb neural circuits and measure the circuit's response. One recent advance is the use of optogenetic tools to perturb neural circuits, particularly neural circuits with cell-type specificity. Optogenetics creates light-sensitive ion channels for optical stimulation of neural assemblies, and therefore allow experimenters or medical practitioners to selectively excite neural channels and/or inhibit other neural channels with high precision. Optogenetic technology is driving demand for new techniques and products to couple light stimulation with high-density neural recordings. Intracortical opto-electrical devices or "optrodes" provide the ultimate combination of perturbation and monitoring capabilities. However, the technology and application of conventional optrode devices are raw and inefficient. Commercial systems are not available and current techniques have limitations in most experiments. For instance, many neuroscientists modify commercially available optical fibers for use in their optogenetic studies, but these have drawbacks that limit practical applications, including having only one-dimensional light output, and being brittle and dangerous due to being made of fused silica. Furthermore, an electrical artifact, known as the Becquerel or photoelectrochemical effect, arises when an electrode is placed in a conductive medium and illuminated even at low intensity. In the Becquerel effect, incident light produces a current that affects low frequency potentials, thereby confounding some neural recording applications.

Thus, there is a need in the neural interface field, which includes the clinical treatment of neurological disorders, to create an improved waveguide neural interface device. This invention provides such an improved waveguide neural interface device.

BRIEF DESCRIPTION OF THE FIGURES

FIG. 1A is a front schematic view of one variation of a waveguide neural interface device 100 according to the present invention;

FIGS. 1B to 1D are side schematic views of various embodiments of waveguide neural interface devices according to the present invention;

FIG. 2 is a side schematic view of the neural interface device 100 shown in FIG. 1;

FIGS. 14A-14D are schematics of the waveguide component, the neural device component, and two possible assembled perspective views, respectively, of the waveguide neural interface device of a second preferred embodiment;

DESCRIPTION OF THE PREFERRED EMBODIMENTS

Figure 3A:
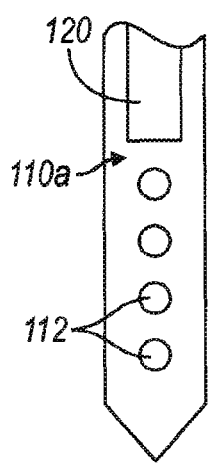
FIGS. 3A and 3B are front and side schematic views, respectively, of another variation of a waveguide interface device according to the present invention.

The following description of preferred embodiments of the invention is not intended to limit the invention to these preferred embodiments, but rather to enable any person skilled in the art to make and use this invention. As used herein and unless stated otherwise, the term "dissipation" (and its derivatives) is used to refer to the dissipation of light as a result of diffusion, scattering (e.g., single event scattering or multiple event scattering), or any suitable emission or redirection of light.

1. Waveguide Neural Interface Device of a First Preferred Embodiment

As shown in FIGS. 1 and 2, the waveguide neural interface device 100 of a first preferred embodiment includes: a neural device 110 implantable in tissue and including an array of electrode sites 112 that electrically communicate with their surroundings, in which the array of electrode sites 112 includes at least one recording electrode site; and a waveguide 120 coupled to the neural device that includes a light directing element 122 that carries light along a longitudinal axis and redirects carried light to illuminate selectively targeted tissue. The waveguide 120, which is preferably formed separately from the neural device 110, redirects at least a portion of the carried light laterally away from the longitudinal axis, and the recording electrode site is preferably configured to sample illuminated tissue. The waveguide neural interface device of this embodiment provides greater flexibility and functionality to the design space of neural electrical-optical devices, or "optrodes". The waveguide neural interface device may provide a one-dimensional optical stimulation pattern (e.g., FIGS. 1 and 3-6), or at least a two-dimensional optical stimulation pattern (e.g., FIGS. 10 and 11). The waveguide neural interface device preferably provides such optical stimulation patterns with neural recording capabilities for applications of optogenetic techniques. For example, the device may enable the control and monitoring of neural activity with spatial selectivity, and temporal resolution and duration that are useful for clinical treatment and mechanistic investigation of neural assemblies. The waveguide neural interface device 100 is preferably used to provide optical stimulation and neural monitoring in clinical applications (e.g., treatment of Parkinson's disease, epilepsy, depression, obesity, hypertension, but may be used in any condition where stimulation is useful as a treatment, or any suitable condition) and/or in any suitable research applications (e.g., for linking and mapping behavior to the collective activity of neural assemblies). Combining highly specific 2D and 3D neural probes (having electrical sensing and/or stimulation) with optical sensing and/or stimulation may significantly increase possible experimental and clinical applications. The waveguide neural interface device is preferably insertable or implantable in neural tissue, and more preferably brain tissue, but may be used with any suitable tissue.

The neural device 110 functions to provide structure for the array of electrode sites 112, and in some cases, for insertion and/or implantation of the waveguide neural interface device into tissue. The neural device 110 may be a neural probe such as that described in U.S. Patent Application number 2008/0208283, which is included in its entirety by this reference. Alternatively, the neural device 110 may be any suitable neural probe or suitable structure. As shown in FIGS. 1-9, the neural device 110 includes an electrode substrate and an array of electrode sites 112 coupled to the electrode substrate. The array of electrode sites 112 preferably includes one or more recording electrode sites that sample illuminated tissue, and may further include one or more stimulation electrode sites that provide electrical stimulation. At least a portion of the array of electrode sites 112, particularly the recording electrode sites, are preferably located adjacent to the light directing element 122 of the waveguide 120, in a manner to avoid direct illumination on the electrode site, thereby reducing or eliminating impact of the Becquerel effect on signals obtained through the neural interface device and improving the accuracy of data collection in the neural interface device. The neural device 110 is preferably substantially planar and includes a front face and a back face behind or opposite the front face. Although the front and back faces are preferably flat, the neural device 110 may alternatively have a curved shape, such as one in which the front and/or back faces are concave, convex, or wavy. In an alternative version, the neural device 110 is approximately cylindrical and the electrode sites 112 are arranged axially along and/or circumferentially around the neural device. The neural device 110 may alternatively have any suitable shape or cross-section, such as elliptical or rectangular. The neural device may be flexible (e.g., may include a flexible interconnect coupled to an electrode substrate) or rigid (e.g., electrode substrate coupled to a rigid backing, rigid carrier, or other rigid structure).

Figure 6A:
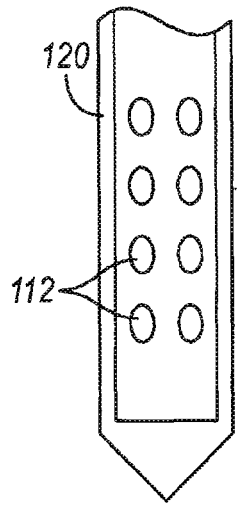
FIGS. 6A and 6B are front and side schematic views, respectively, of another variation of a waveguide interface device according to the present invention.
Figure 6B:
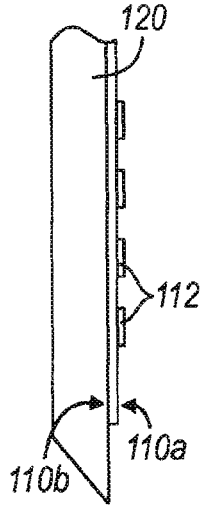

The waveguide 120 functions to redirect light away from the waveguide neural interface device to optically stimulate targeted tissue. In some embodiments, as shown in FIG. 6, the waveguide 120 may further function as a carrier or other structure for providing structural support of the waveguide neural interface device for insertion into tissue. In these embodiments, the waveguide 120 is preferably rigid or rigid enough to provide support for insertion into tissue. For example, the neural device 110 may be a flexible neural probe substrate, with the waveguide 120 relatively thick and rigid and the neural probe substrate relatively thin and/or flexible. The waveguide 120 may be tapered, narrowing towards a distal end of the waveguide, to reduce tissue damage during insertion into the tissue. The waveguide 120 preferably receives light along its longitudinal axis from a light source, but may alternatively receive light in any suitable manner. For receiving light, the waveguide may have a relatively large cross-section for mating to an optical connector that provides the light. The waveguide 120 may carry the light through internal reflection, or any suitable method. The waveguide 120 may be rigid, semi-rigid, or flexible. The waveguide 120 is preferably a thin-film structure such as one formed by one or more of several suitable fabrication processes including: micro-opto-electro-mechanical systems (MOEMS), photolithography, microembossing, thermal nanoimprint lithography (NIL), combined nanoimprinting and photolithography (CNP), and/or any suitable fabrication process. Example waveguide materials for these fabrication techniques include but are not limited to organic materials such as SU-8, Poly(methyl methacrylate) (PMMA), perfluoropolymers, polydimethylsiloxane (PDMS), parylene, and/or inorganic materials such as silicon dioxide ($SiO_2$), silicon nitride, silicon oxynitride, and silica. However, the waveguide may alternatively be an optical fiber or any suitable light-carrying waveguide made of any suitable material.

As shown in FIGS. 1-6, the waveguide 120 preferably includes a light directing element 122 that directs light laterally away from the longitudinal axis of the waveguide (i.e., the directed light is aimed or travels in a direction having a nonzero component perpendicular to the longitudinal axis of the waveguide). The light directing element 122 may be one or more of several variations, including one or more features that refract, reflect, focus, and/or scatters light, and/or perform any suitable manipulation of light. In a preferred embodiment, the waveguide 120 further includes an inner core and a cladding layer over the core, and the core and cladding material preferably facilitate internal reflection along the waveguide. The waveguide may undergo photolithographic processes to pattern the cladding and selectively expose the core, such that the light directing portion of the waveguide includes the exposed core.

In a first variation, as shown in FIG. 1B, the light directing element 122 includes a refractor 122a that refracts carried light away from the waveguide 120 at a particular angle of refraction. The refractor may be located at a distal end of the waveguide. For example, the distal end may include an angled tip whose shape is configured to refract light carried by the waveguide. As another example, the distal end may additionally and/or alternatively include material having a different index of refraction than the rest of the waveguide. The refractor 122a may additionally and/or alternatively be located at any suitable location along the length of the waveguide 120. For example, as shown in FIG. 2, the waveguide may include one or more angled refractors 122a that each distributes a portion of the carried light away from the waveguide 120 through refraction. The light directing element may include any suitable number of refractors of any suitable size or shape.

Figure 4A:
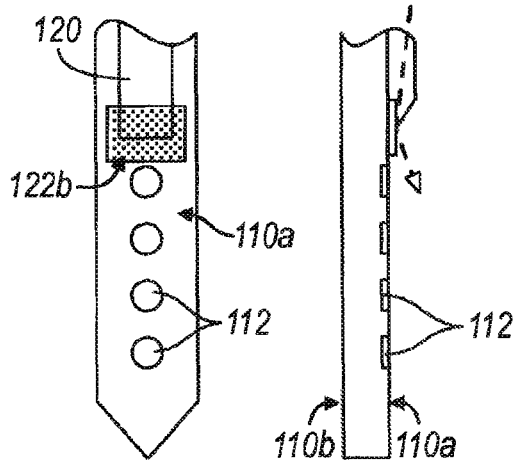
FIGS. 4A and 4B are front and side schematic views, respectively, of another variation of a waveguide interface device according to the present invention.

In a second variation, as shown in FIGS. 1C and 4A, the light directing element includes a reflector 122b that reflects carried light away from the waveguide 120 or back along the longitudinal axis. The reflector 122b may be a thin film of reflective metal, a mirror, or any suitable kind of reflector. The surface roughness of this reflector may be increased or decreased to modulate the directionality or focus of the light path. The reflector may be located at a distal end of the waveguide 120. For example, the distal end of the waveguide may include a reflector that is angled to reflect carried light away from the waveguide at a certain angle. As another example, the distal end of the waveguide may include a reflector 224 (FIG. 14A) that reflects carried light back in a proximal direction along the longitudinal axis, which may be useful to recapture light that "misses" or bypasses other light directing elements. In this example, the reflected light, which otherwise would be lost, is preferably given another opportunity to be directed away from the waveguide 120 by another light directing element, thereby increasing efficiency of the waveguide neural interface device. The reflector 122b may additionally and/or alternatively be located at any suitable location along the length of the waveguide. The light directing element may further include any suitable number of reflectors.

In a third variation, as shown in FIG. 1D, the light directing element includes a lens 122c that focuses light to a point away from the waveguide 120. The lens 122c, which may be a tubular lens or any suitable lens, is preferably configured to converge carried light to a focal point outside of the waveguide 120, diverge the carried light, or direct the carried light in any suitable manner. The lens may have a focal length preselected to focus light to targeted tissue. Alternatively, the lens may have an adjustable and/or variable focal length that enables the lens to focus light at an adjustable distance away from the waveguide, thereby providing another dimension of control of tissue targeting. Examples of adjustable lens include temperature-controlled lens (e.g., liquid crystal lens) and voltage-controlled lens (e.g., ferroelectric lens). The light directing element may further include any suitable number of lenses which may be manufactured separately and modularly assembled inside the opening in the device aperture 114.

In a fourth variation, the light directing element 122 includes a scattering element that scatters carried light away from the waveguide 120 or back along the longitudinal axis, in applications similar to the reflector. The scattering element may include a distributed Bragg reflector, surface corrugations, an optically dissipating coating, optically dissipating molecules embedded in the waveguide 120, and/or any suitable kind of scattering element. The light directing element may further include any suitable number of scattering elements.

The waveguide 120 may include one or more light directing elements 122, and where there are multiple light directing elements, the light directing elements may be one or more of the variations in any suitable combination. Furthermore, the waveguide 120 may include an arrangement of a plurality of light directing elements longitudinally and/or laterally along the waveguide in any suitable pattern, thereby distributing carried light away from the waveguide in any suitable manner. Each light directing element may redirect a portion of the carried light from a different point on the waveguide. In particular, each light directing element may redirect a portion of the carried light at a different distance along the length of the waveguide.

In some variations, the waveguide 120 may further include a filter, such as one that allows only a certain bandwidth of light to pass. For example, in applications in which only a portion of illuminated tissue is configured to be stimulated by a certain color or wavelength, the filter allowing that color or wavelength to pass may consequently allow only the receptive portion of illuminated tissue to be stimulated, thereby providing another dimension of tissue targeting.

The waveguide neural interface device may include any suitable combination of the neural device 110, waveguide 120, and one or more light directing elements 122. In a first variation of the waveguide neural interface device, as shown in FIGS. 1A-1D, the array of electrode sites 112 is located on a front face 110a of the neural device 110, and the waveguide 120 is coupled to or mounted on a back face 110b of the neural device 110, where the front face 110a of the neural device may be any suitable face of the neural device (and may be defined as any face including at least a portion of the array of electrode sites) and the back face 110b is on an opposite side of (or "behind") the front face. In this variation, the neural device 110 preferably includes an aperture 114 that extends between the back face and front face. The aperture 114 is preferably a through hole, but may include any suitable aperture such as a grating, a mesh-like structure, filter, or any suitable structure that permits passage of light. The aperture may additionally and/or alternatively include a translucent material that permits passage of light from the waveguide. The array of electrode sites 112 and the light directing element 122 are preferably located relative to the aperture 114 such that the light directing element of the waveguide 120 redirects light through the aperture 114 to illuminate tissue adjacent to the electrode sites. For example, as shown in FIG. 1A, the array of electrode sites 112 may be arranged around the perimeter of the aperture 114. The light directing element 122 may include a refractor that refracts light through the aperture of the neural device, a reflector that reflects light through the aperture of the neural device, and/or a lens that focuses light through the aperture. The neural device 110 may include additional apertures that are distributed along the length of the neural device and corresponding to a light directing element.

Figure 3B:
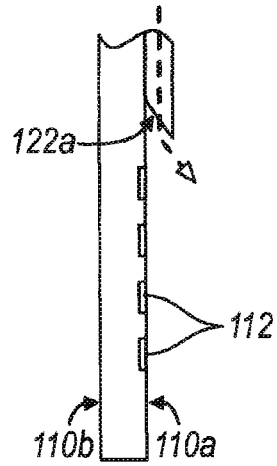
Figure 4B:
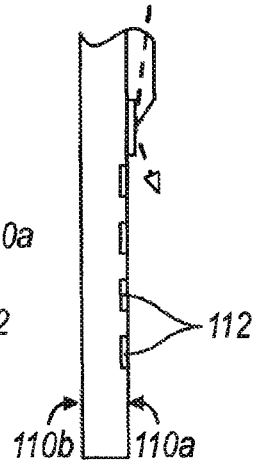

In a second variation of the waveguide neural interface device, as shown in FIGS. 3 and 4, the array of electrode sites 112 is located on the front face 110a of the neural device 110 and the waveguide 120 is coupled to or mounted on the front face of the neural device adjacent to the array of electrode sites 112. The waveguide 120 may include one or more of any combination of light directing element variations. For example, the front-mounted waveguide includes a refractor 122a and/or reflector 122b light directing element on the distal end of the waveguide that refracts and/or reflects light at an angle that illuminates tissue adjacent to the array of electrode sites 112. As another example, as shown in FIG. 2, the waveguide 120 may include one or more light directing elements positioned along the length of the waveguide, such that each light directing element distributes at least a portion of the carried light away from the waveguide 120 through refraction, reflection, a lens, or any suitable light directing element.

Figure 5A:
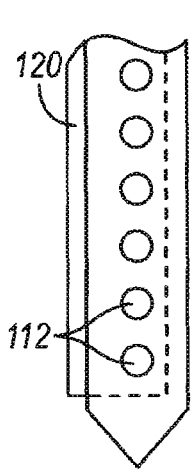
FIGS. 5A and 5B are front and side schematic views, respectively, of another variation of a waveguide interface device according to the present invention.
Figure 5B:
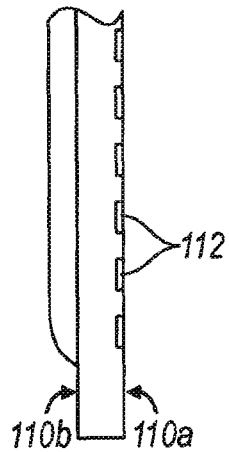

In a third variation of the waveguide neural interface device, as shown in FIG. 5, the waveguide 120 extends laterally beyond the electrode substrate or other portion of the neural device 110. In this variation, the light directing element may extend laterally beyond the neural device, and include any of the refractor, reflector, lens, and/or scattering element variations as described above, or any suitable variation of a light direction element.

Other variations of the waveguide neural interface device include any suitable combination of the above variations, such as one in which the array of electrode sites 112 is located on the front face of the neural device 110 and the waveguide 120 is both coupled to the back face of the neural device having an aperture and extends laterally beyond a portion of the neural device, such that some carried light is directed away from the waveguide 120 through the aperture and some carried light is directed away from the waveguide from the lateral extension.

The waveguide 120 is preferably formed separately from the neural device 110, and coupled to the neural device 110 during assembly as described below. However, the waveguide may alternatively be integrally formed with the neural device (such as at the wafer level during fabrication of the waveguide neural interface device).

Figure 7:
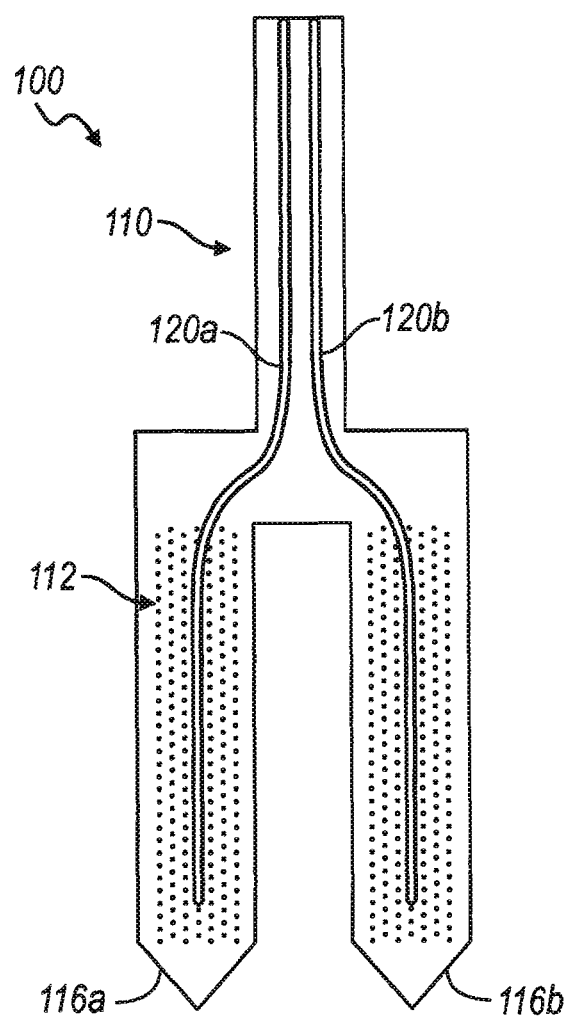
FIGS. 7 and 8 are schematics of branched variations of the waveguide neural interface device of the first preferred embodiment.
Figure 8:
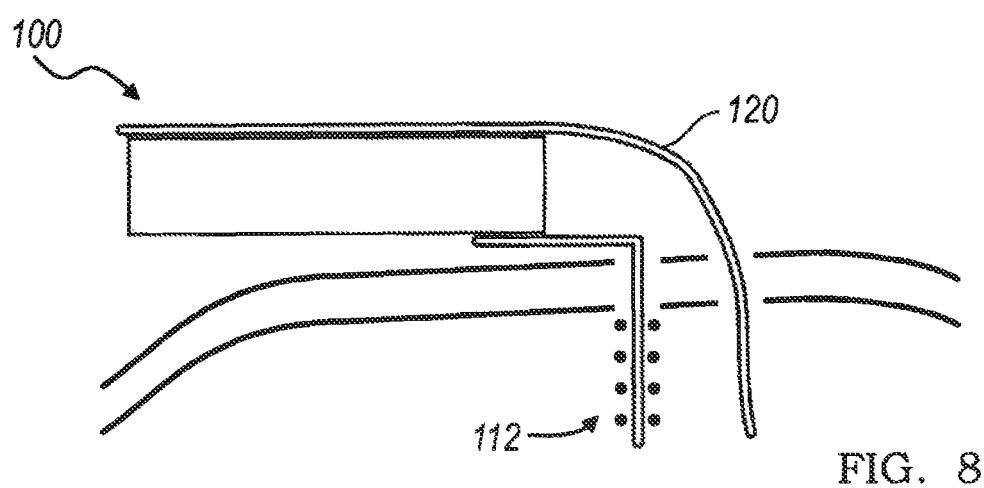
Figure 9A:
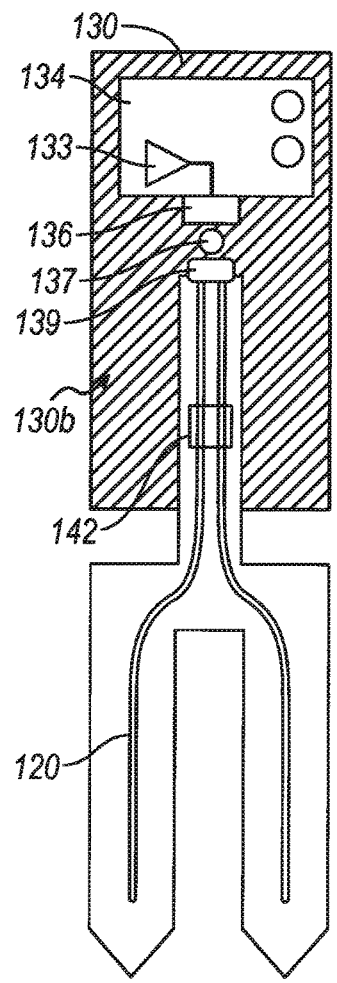
FIGS. 9A-9C are front, side, and back view schematics, respectively, of the circuit board of the waveguide neural interface device of a preferred embodiment.
Figure 9B:
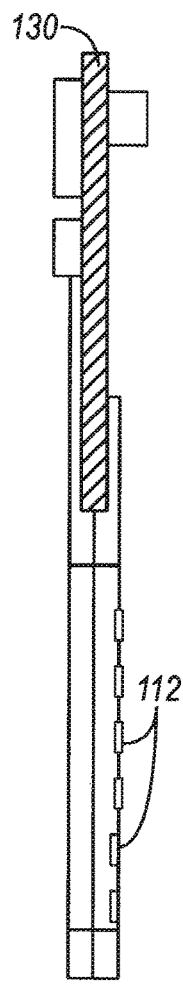
Figure 9C:
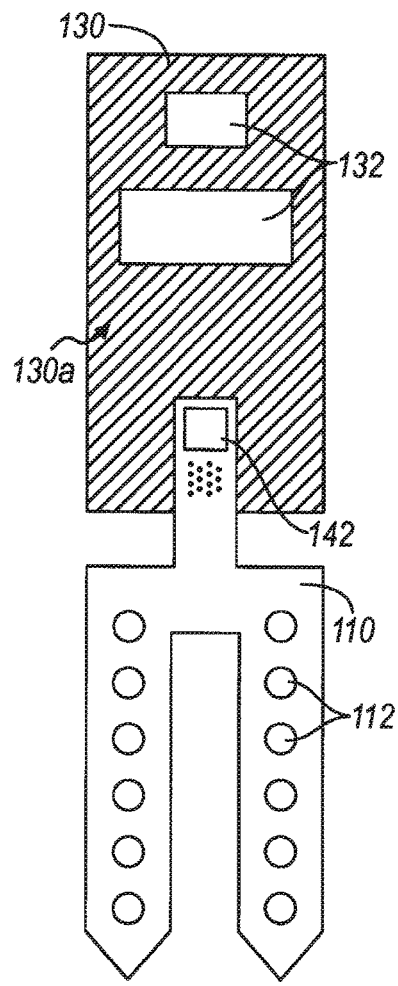
Figure 9D:
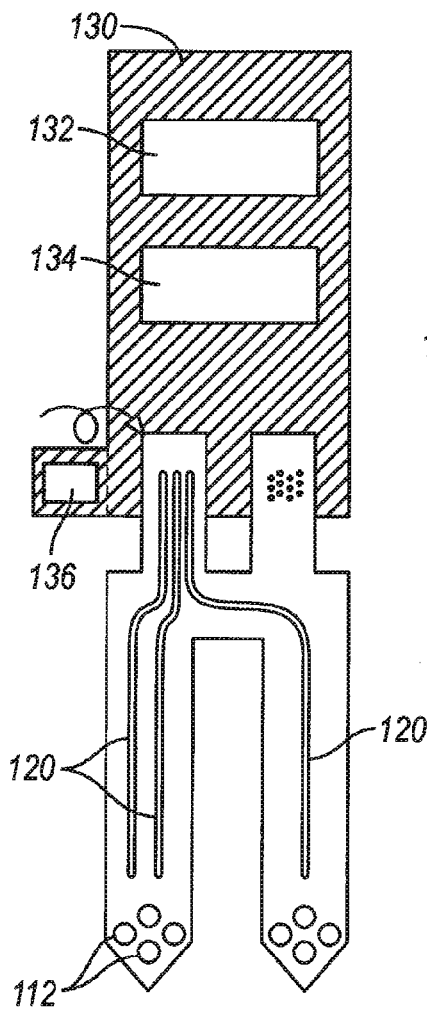
FIGS. 9D and 9E are schematics of variations of the circuit board of the waveguide neural interface device of a preferred embodiment.

In some embodiments, the waveguide neural interface device may include multiple branches and/or multiple waveguides configured to interface with different targeted regions of tissue. The modular integration of multiple branches, multiple waveguides, and/or multiple arrays of electrode sites enables targeting of different regions of tissue while reducing overall size and footprint of the equipment and potentially reducing external connections to a single external connection. For example, as shown in FIG. 7, the neural device 110 may include a first branch 116a and a second branch 116b, in which a first waveguide 120a is coupled to the first branch and a second waveguide is coupled to the second branch. Additional waveguides may be distributed on the first, second, or more branches of the neural device in any suitable manner (e.g., two waveguides on one branch and a third on another branch, as shown in FIG. 9D). The branches may be positioned front to back relative to each other and/or side to side relative to each other (FIG. 7), or in any suitable orientation. As another example, as shown in FIG. 8, the neural device 110 may include a first branch and a second branch passing through different access points in the skull, in which the array of electrode sites 112 (or a subset of the array of electrode sites, such as a portion that includes stimulation electrode sites and/or some recording electrode sites) is coupled to the first branch and the waveguide is coupled to the second branch. The branches of the neural device 110 may be flexible or rigid, such as on a flexible or rigid substrate. Alternatively, a portion of the branches on a single neural device may be flexible, while another portion of the branches may be rigid.

The waveguide neural interface device preferably further includes a circuit board 130 that interfaces with at least one of the array of electrode sites 112 and the waveguide 120. As shown in FIGS. 9A-9C, the circuit board is preferably double faced (or "double sided") and includes an electrical face 130a having electrical components 132 that interface with the array of electrode sites 112 and an optical face 130b having optical components 134 that interface with the waveguide 120. The circuit board may be a single board with two faces or two boards coupled back-to-back with fasteners, adhesive, or in any suitable manner.

Figure 9E:
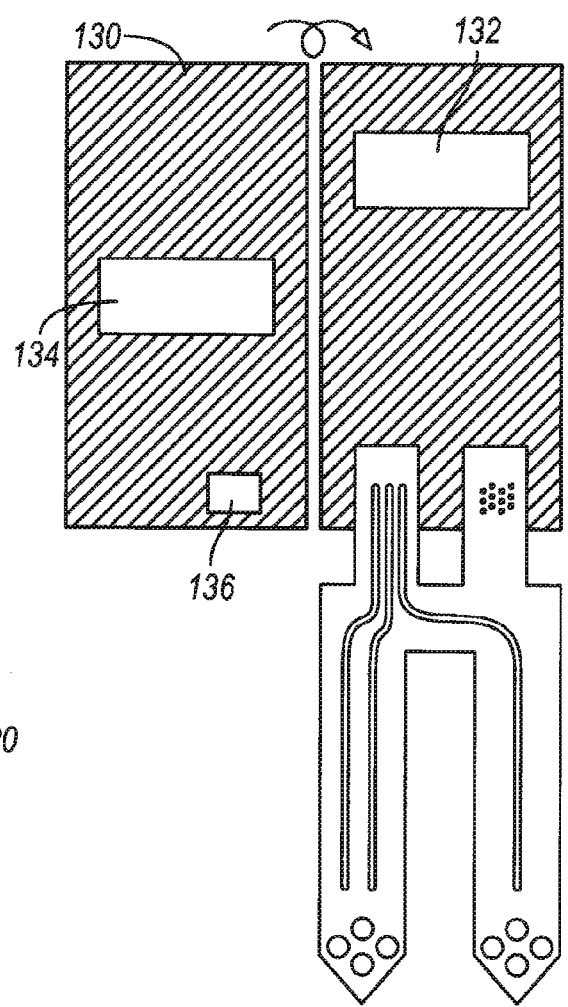

By separating the electrical and optical components, the circuit board may permit maximization of space on the circuit board and reduce noise coupling. The waveguide 120 preferably couples directly to the optical face 130b of the circuit board and the neural device 110 preferably couples directly to the electrical face of the circuit board. This "modular" coupling assembly may be aided by features to improve component alignment, such as fiducial marks, tabs, and/or corresponding alignment holes 142. Alternatively, as shown in FIG. 9D, the circuit board may include an electrical region having electrical components 132 and an optical region having optical components 134, in which both the electrical and optical regions are located on the same face or side of the circuit board 130. In another variation, each face of the circuit board may include a mixture of electrical and optical components (i.e., each face includes a portion of the total electrical components and a portion of the total optical components). In one variation, the circuit board may include folding portions that fold over a main face of the circuit board. For example, a folding portion may include a light source 136 that, when the folding portion is folded over the main face of the circuit board, meets and couples to a waveguide 120. In another variation, as shown in FIG. 9E, the circuit board may include two faces that sandwich the waveguide and/or neural device (the circuit board may fold or include two separate sandwiching pieces), which may advantageously allow modular construction of the circuit board and reduce noise coupling or other incidental interactions on the circuit board. The electrical components 132 preferably include various passive or active electrical components, bond pads for the array of electrode sites, a connector for interfacing the neural device 110 to external components (e.g., a flexible interconnect that carries electrical lines for the array of electrode sites), current driver 133 for a diode or LED, control electronics for providing a control signal, a battery power source, and/or any suitable electronics. The optical components 134 preferably include one or more light collecting elements 137, light focusing elements 139, optical filters, and/or any suitable optical components. The optical face may further include one or more light sources coupled to the waveguide or waveguides. The light source 136 may be a circuit board-mounted light-emitting diode (LED), a laser diode, a vertical cavity surface-emitting laser (VCSEL), or any suitable laser or light source. However, the light source may be an external light source such as a laser, laser diode, or one or more LEDs. Coupling light from an external light source or from a circuit board-mounted light source may be accomplished using one or more techniques, and the number of coupling options is increased by using modular components 110 and 120. For example, coupling the light source and the waveguide may involve mounting any number of collecting elements 137 (e.g., spherical lens, biconvex lens, plano-convex lens) and focusing elements 139 (e.g, gradient index (GRIN) lens, spherical lens, biconvex lens, plano-convex lens) between the light source and the waveguide. Coupling may also use butt coupling that directly couples the light source and the waveguide. Surface emitting LEDs may be mounted vertically (e.g., DIP socket on a "surf" board) or horizontally on the same circuit board and rely on reflective elements to direct the path into one or more longitudinally mounted waveguides. However, any suitable coupling means may be used to couple the light source to the one or more waveguides.

Fabrication of the waveguide 120 preferably further includes releasing the waveguide from the substrate through any suitable process, and cut to a suitable, predetermined length. The process of building, releasing, then cutting the waveguide 220 may be useful to improve modularity of the process and/or customizations of specific waveguide neural interface devices, such as for the specific customization of shape and distribution of the optically portions and dimensions of the overall waveguide. The light directing elements 122 may also be controlled and formed in the process of cutting or etching the waveguide to create various tip profiles and angles.

2. Waveguide Neural Interface Device of a Second Preferred Embodiment

Figure 10:
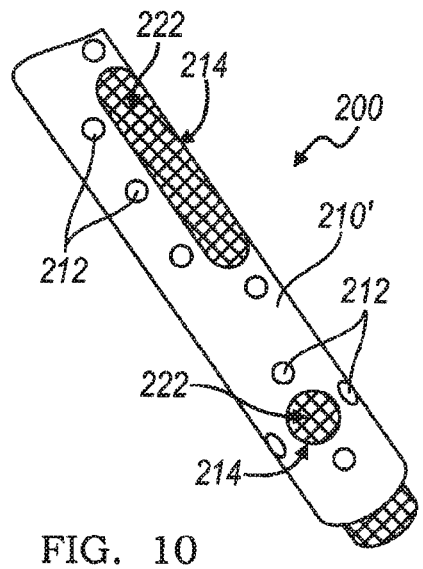
FIG. 10 is a schematic of one variation of the waveguide neural interface device of a second preferred embodiment.

As shown in FIGS. 10 and 11, the waveguide neural interface device 200 of a second preferred embodiment includes: a neural device 210 implantable in tissue and including an array of electrode sites 212 that electrically communicate with their surroundings, in which the array of electrode sites includes at least one recording electrode site, and a waveguide 220 coupled to the neural device 210 that carries light along a longitudinal axis and includes an optically dissipating portion 222 that dissipates the carried light to illuminate selectively targeted tissue. At least a portion of the dissipated light preferably travels laterally away from the longitudinal axis from the optically dissipating portion 222, and the recording electrode site is preferably configured to sample illuminated tissue which may be electrically excited by the illumination. The waveguide neural interface device of the second preferred embodiment is preferably used in a similar manner as the first preferred embodiment.

The neural device 210 of the second preferred embodiment is preferably similar to the neural device 110 of the first preferred embodiment. The neural device 210 preferably includes an electrode substrate that is layered over the waveguide 220, and the electrode substrate preferably includes at least a portion of the array of electrode sites 212.

The waveguide 220 of the second preferred embodiment of the waveguide neural device functions to redirect light away from the waveguide neural interface device to optically stimulate targeted tissue. The waveguide 220 of the second preferred embodiment of the waveguide neural interface device may be similar to that of the first preferred embodiment. The waveguide 220 may be cylindrical (e.g., an optical fiber or other cylindrical waveguide, as in FIG. 10), substantially planar (e.g., a thin-film waveguide, as in FIG. 11A), or any suitable shape. In this embodiment, the waveguide 220 preferably includes one or more optically dissipating portions 222 that dissipate light away from the waveguide neural interface device. The optically dissipating portions 222 may be elongated "light ports" that are substantially rectangular, elliptical, circular, or any suitable shape. The particular shape and distribution of optically dissipating portions may depend on the specific application and desired customization. As shown in FIG. 11B, the dissipated light preferably travels laterally away from the longitudinal axis of the waveguide 220 (i.e., the dissipated light travels in a direction having a nonzero component perpendicular to the longitudinal axis of the waveguide). The dissipated light preferably has substantially uniform intensity as a function of distance along the waveguide 220, and preferably as a function of distance along the optically dissipating portion. As shown in FIGS. 12A and 12D, conventional optical fiber optrodes provide light axially in only one dimension from one end of the optical fiber, which results in uncontrolled scattering, conical spreading and a rapidly declining intensity as a function of distance along the waveguide (i.e. depth of the device when inserted into tissue). In contrast, as shown in FIGS. 12B-12D, the waveguide neural interface device described herein preferably enables at least two-dimensional light with controlled scattering and a uniform intensity as a function of distance along the waveguide, although in some alternative embodiments the device may provide light in any suitable pattern of distribution and/or intensity.

The waveguide 220 includes an inner core 230 and a cladding layer 232 over the core, and the core and cladding material are preferably selected such that the core and cladding cooperate to facilitate internal reflection. The waveguide 220 preferably undergoes photolithographic processes to pattern the cladding and selectively expose the core, such that the optically dissipating portion 222 of the waveguide includes the exposed core. However, the optically dissipating portion 222 may alternatively be formed in any suitable manner. The optically dissipating portion may include a dissipating material to further define the amount of light diffusion. The amount of light diffusion that the optically dissipating portion 222 provides is at least partially dependent on the amount of surface roughness of the core, the specific properties of the dissipating material, width of the optically dissipating portion relative to the total waveguide width, and waveguide thickness. During fabrication, many if not all of these parameters can be closely controlled, providing for precise specificity in waveguide features and detailed customization of the waveguide neural interface device for a variety of applications.

Figure 13A:
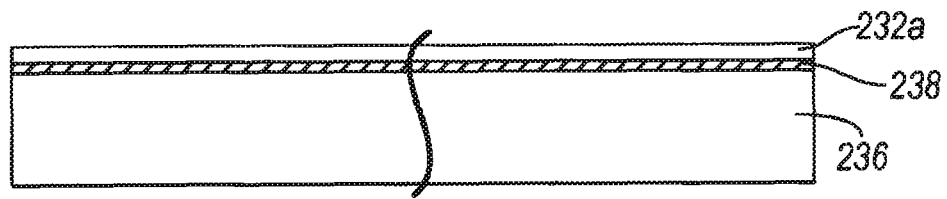
FIGS. 13A-13D are schematics of the fabrication process of a thin-film waveguide of the waveguide neural interface device of a second preferred embodiment.
Figure 13B:
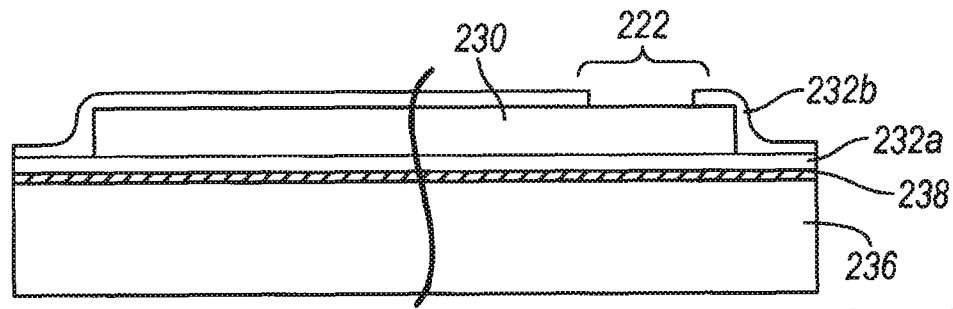
Figure 13C:
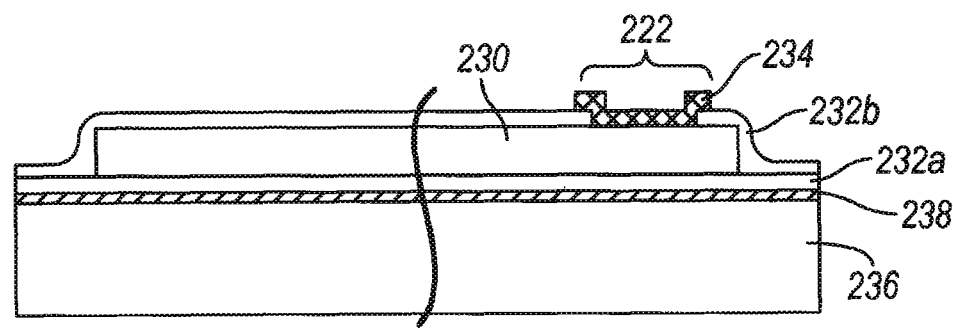
Figure 13D:
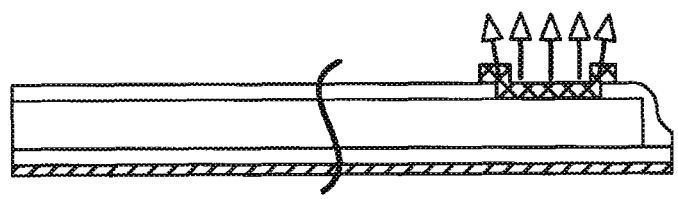

In one variation of a waveguide fabrication process, as shown in FIG. 13A, a sacrificial layer of material 238 is deposited onto a substrate 236, and a lower cladding layer 232a of cladding material is deposited (e.g. through CVD, PECVD, spinning processes or any suitable deposition process) onto the sacrificial layer. As shown in FIG. 13B, the core material is deposited onto the structure and patterned to form the inner core 230. An upper cladding layer 232b of cladding material is deposited over the core 230, followed by deposition and patterning of a hard mask. The upper cladding layer 232b is preferably patterned with a suitable patterning process that selectively removes the upper cladding layer 232b and/or roughens the core surface to form the optically dissipating portion 222. The exposed core surface may additionally and/or alternatively be texturized in any suitable manner to form the optically dissipating portion 222. The optional, controlled addition of a dissipating medium (e.g, diffusive and/or scattering material) to the exposed core may further affect the amount of light dissipation that the optically dissipating portion provides. In one variation, as shown in FIG. 13C, a coating layer 234 of a light dissipating material (e.g., aluminum oxide, titanium dioxide, diamond powder, or any suitable material) may be deposited and patterned over the exposed core. For example, the addition of an optically dissipating material may be similar to that described in U.S. Pat. Nos. 5,946,441 and 5,580,932, which are incorporated in their entirety by this reference. The dissipating material is preferably biocompatible, has a refractive index greater than that of the waveguide core, and has low optical absorption. In another variation, molecules of the light dissipating material may be embedded in the exposed core using ion implantation or diffusion or any appropriate means of embedding. Furthermore, wavelength-sensitive light dissipating molecules could be applied to different "ports" in the waveguide at various locations to selectively control light emission as a function of wavelength (e.g., provide spatial control of light output for another dimension of customization), such as that described in U.S. Pat. No. 7,194,158, which is incorporated in its entirety by this reference.

Depositing and patterning the optically dissipating layer may alternatively be performed before depositing the upper cladding layer of cladding material. Fabrication of the waveguide 220 preferably further includes releasing the waveguide from the substrate through any suitable process, and cut to a suitable, predetermined length. The process of building, releasing, then cutting the waveguide 220 may be useful to improve modularity of the process and/or customizations of specific waveguide neural interface devices, such as for the specific customization of shape and distribution of the optically dissipating portions and dimensions of the overall waveguide. Alternatively, the final length of the waveguide 220 may be etched with another hard mask prior to release from the substrate. In some preferred embodiments, the overall length of the waveguide 220 may be between 3-400 mm long and/or up to 200 µm in thickness, depending on the application.

In one specific example, a waveguide includes a core of SU-8 (supplied by MicroChem) and cladding layers of Cytop CTL-809M (supplied by Asahi Glass). Cytop includes a lower index of refraction (n=1.34) than SU-8 (n–1.59), such that the combination of the two materials forms a waveguide with internal reflection. The sacrificial layer, lower cladding layer, core, and upper cladding layer are preferably formed as described above. The upper cladding layer is then patterned with an oxygen plasma to expose and roughen the core surface. A dissipating layer of aluminum oxide approximately 300 nm thick is sputter deposited in place of the removed upper cladding layer. The layer of aluminum oxide is then patterned using buffer hydrofluoric (HF) acid. The waveguide is then released from the wafer and diamond-scribed to a desired length. In this example, the waveguide thickness is on the order of approximately 30 µm.

In another variation of a waveguide fabrication process, as shown in FIG. 14, the waveguide 220 is an optical fiber with an internal core 230 and an outer cladding layer 232 around the core. Similar to the first variation of a waveguide fabrication process, the cladding layer is preferably patterned to selectively remove the cladding layer to expose and/or roughen the core surface. The exposed core surface may additionally and/or alternatively be texturized in any suitable manner to form the optically dissipating portion. The optional, controlled addition of a dissipating coating and/or embedded dissipating molecules to the core surface may further define the optically dissipating portion. Additional alternative processes for creating the waveguide 220 are described in U.S. Pat. No. 5,946,441, entitled "Light-diffusing device for an optical fiber, methods of producing and using same, and apparatus for diffusing light from an optical fiber", which is incorporated in its entirety by this reference.

The electrode substrate of the neural device 210 is preferably layered over the waveguide 220, and more preferably in such a manner that the optically dissipating portion of the waveguide is adjacent to at least a portion of the array of electrode sites. The waveguide neural interface device may include any suitable combination of the neural device 210 and waveguide 220. As shown in FIGS. 10 and 14, in a first variation, the electrode substrate is wrapped around the waveguide 220. In this variation, the electrode substrate preferably includes at least one aperture 214 that corresponds to the optically dissipating portion 222 of the waveguide 220 such that the dissipated light is scattered through the aperture 214 to illuminate tissue. The aperture 214 may be formed in the neural device 210 prior to wrapping around the waveguide 220, or may be formed after wrapping around the waveguide. Furthermore, the optically dissipating portion 222 may be formed in the waveguide 220 before or after wrapping the electrode substrate around the waveguide. At least a portion of the array of electrode sites 212 is preferably near or adjacent to the aperture 214 such that at least one recording electrode site is configured to sample illuminated tissue. The aperture 214 may be substantially rectangular, circular, elliptical, or any suitable shape. As another example, the aperture 214 may be elongated in the direction of the longitudinal axis of the waveguide, as shown in FIG. 10. The aperture 214 of the electrode substrate is preferably similar in shape and size to an underlying optically dissipating portion 222 of the waveguide 220, but the aperture may alternatively be smaller or larger than the optically dissipating portion 222. The electrode substrate may be permanently attached to the waveguide 220 such that its position relative to the waveguide is fixed. Alternatively, the electrode substrate may be non-permanently attached to the waveguide, such that the neural device is adjustable along the length and/or in rotation around the waveguide 220, such that the aperture 214 acts as a movable window that selectively allows light from the optically dissipating portion, thereby adding another dimension of customization. The dissipated light preferably has substantially uniform intensity as a function of distance along the aperture 214. Further, the electrode substrate may include multiple apertures, each corresponding to an optically dissipating portion. The number of apertures in the electrode substrate may be less than, equal to, or greater than the number of optically dissipating portions. In one method of fabrication, the cladding removal and aperture 214 may be created simultaneously using laser ablation, followed by the deposition of the diffusive medium. Alternatively, the cladding removal and aperture formation may occur separately using any suitable technique such as ablation or selective etching.

In another variation, a dissipative portion 222 may alternatively and/or additionally be deposited or otherwise integrated in the electrode substrate. In this variation, the cladding 232 is selectively removed from the waveguide but the light dissipating material may be realized in the electrode substrate and not directly on the waveguide. Alignment of the diffusive layer to the corresponding cladding occurs during assembly. A transparent adhesive may be applied to improve light coupling to the diffusive region.

Figure 11A:
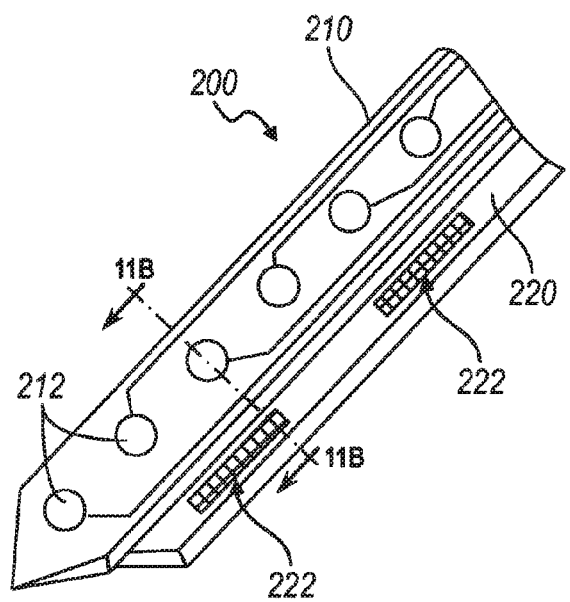
FIGS. 11A and 11B are schematics of a perspective view and cross-sectional view of FIG. 11A taken along line A-A, respectively, of another variation of the waveguide neural interface device of a second preferred embodiment.
Figure 11B:
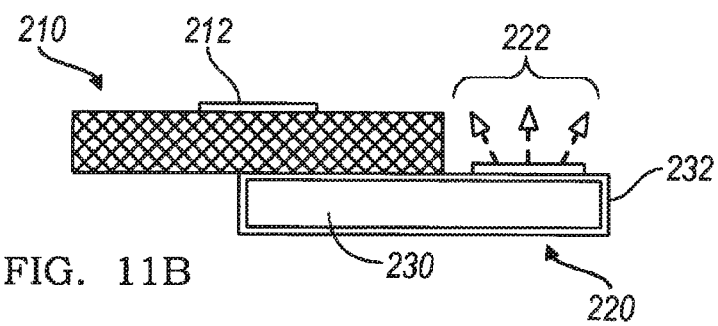
Figure 12A:
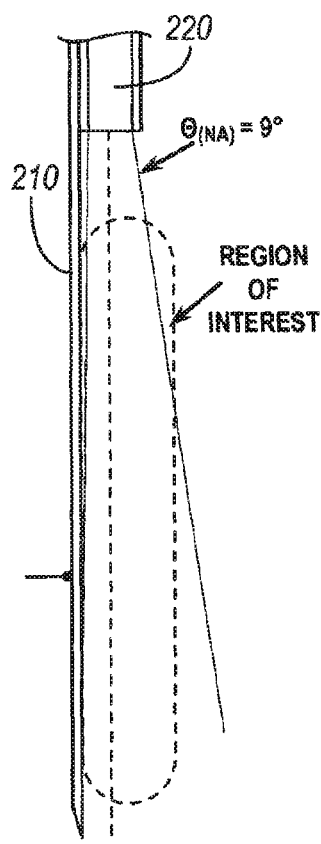
FIG. 12A is a side view schematic of a conventional optrode.
Figure 12B:
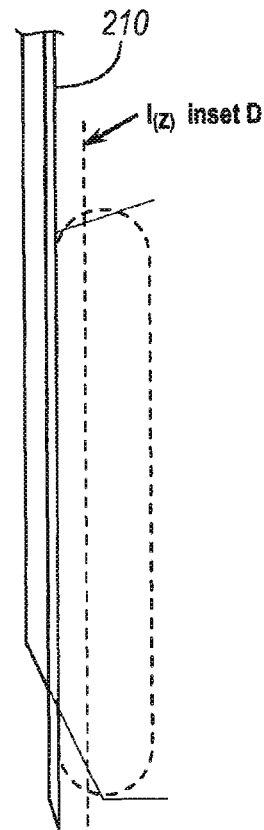
FIGS. 12B and 12C are side view schematics of variations of the waveguide neural interface device of a second preferred embodiment.
Figure 12C:
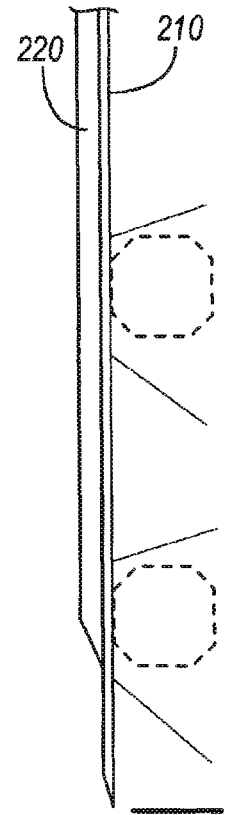
Figure 12D:
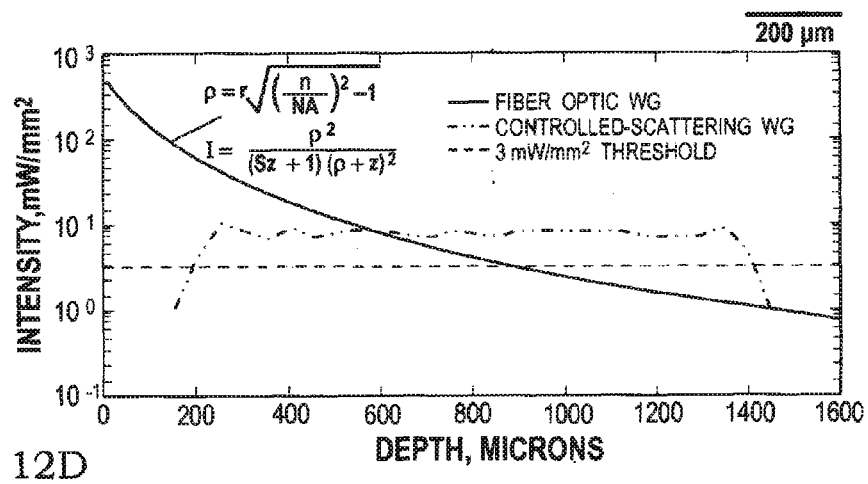
FIG. 12D is a plot of light intensity as a function of depth or longitudinal distance along the waveguide, for a conventional optrode and the waveguide neural interface device of a second preferred embodiment.

In a second variation, as shown in FIG. 11A, the waveguide 220 preferably extends laterally beyond the electrode substrate or other portion of the neural device 210, and more preferably the optically dissipating portion 222 of the waveguide 220 extends laterally beyond the electrode substrate. As shown in FIGS. 12B-12D, the dissipated light preferably travels laterally away from the longitudinal axis of the waveguide 220 and preferably has substantially uniform intensity as a function of distance along the waveguide. In this variation, the waveguide 220 may include a single continuous optically dissipating portion (FIG. 12B) or two or more optically dissipating portions (FIG. 12C) to create discontinuous illumination along the length of the waveguide.

Figure 11C:
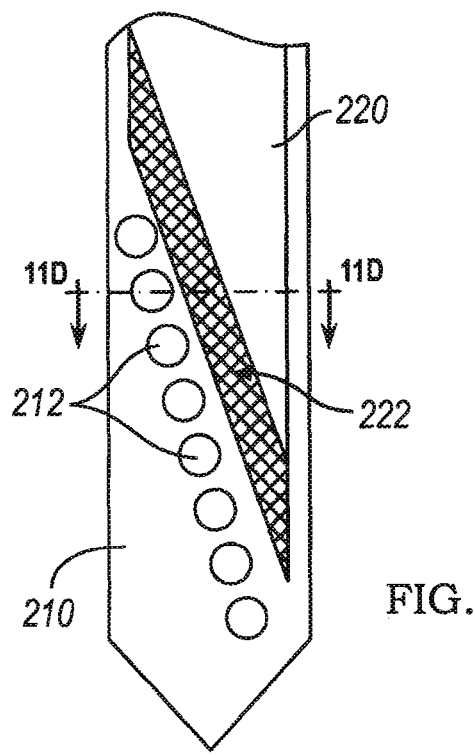
FIGS. 11C and 11D are schematics of a top view and cross-sectional view of FIG. 11C taken along the line B-B, respectively, of another variation of the waveguide neural interface device of a second preferred embodiment.
Figure 11D:
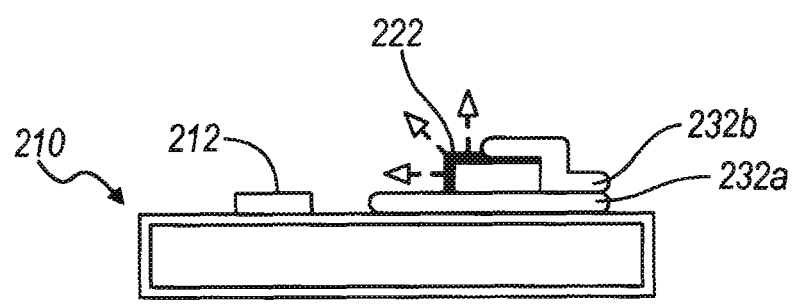

In a third variation, as shown in FIGS. 11C and 11D, the waveguide 220 is preferably mounted on a first side of the device 210 (e.g., the top of the device 210). In this variation, the optically dissipating portion is located on the waveguide that such that optically dissipating portion emits light through the side of the waveguide and/or through the top of the waveguide by diffusing and/or scattering light along the length of at least a portion of the waveguide. The optically dissipating portion may be formed on any suitable edge, side, and/or face to emit light in any suitable direction. Similar to the second variation, the waveguide may include a single continuous optically dissipating portion or two or more separate optically dissipating portions to create discontinuous illumination along the length of the waveguide. One advantage of such a device is to create uniform intensity of light in a local tissue volume near the diffusive element and do so over a relatively long spatial dimension, such as the angled edge shown in FIG. 11C.

As shown in FIG. 14A, the waveguide 220 may further include a reflector tip that reflects carried light along the longitudinal axis. The reflector tip may be similar to that described in the first preferred embodiment of the waveguide neural interface device. By reflecting carried light back along the longitudinal axis, light that otherwise would be lost is returned along the waveguide 220 for potential redirection through the optically dissipating portion, thereby increases efficiency.

Additional variations of the waveguide neural interface device may include any suitable combination of the neural device 210, array of electrode sites, and waveguide 220. For example, the waveguide neural interface device may include both a light direction element of the first preferred embodiment and an optically dissipating portion of the second preferred embodiment.

In some embodiments, similar to that of the first preferred embodiment, the waveguide neural interface device of the second preferred embodiment may include multiple branches and/or multiple waveguides configured to interface with different regions of tissue, and preferably includes a circuit board that interfaces with at least one of the array of electrode sites and the waveguide. The circuit board in the second preferred embodiment is preferably similar to that of the first preferred embodiment.

3. Method of Assembling a Waveguide Neural Interface Device

As shown in FIGS. 15A-15E, the method of making a waveguide neural interface device S300 of a preferred embodiment includes the steps of: providing a neural device that includes a plurality of electrode sites S310; providing a waveguide, separate from the neural device, that is configured to carry light along a longitudinal axis and includes a light directing element that redirects the carried light away from the waveguide S320; providing a circuit board, separate from the neural device and the waveguide, that is configured to interface with the plurality of electrode sites and the waveguide S330; orienting the light emitting element of the waveguide to a predetermined angular orientation relative to the neural device S340, in which the predetermined angular orientation is based on a selected direction of redirected light; and coupling each structure of the group S350 comprising the neural device, the waveguide, and the circuit board to at least one of the other structures in the group, in which coupling includes fixing the waveguide at the predetermined angular orientation relative to the neural device S352.

The method of making the waveguide neural interface device S300 is a modular, cost-effective approach that has several potential advantages. First, the method may provide high spatial resolution, since the waveguide can be rotated along any axis to transform a planar x-y dimension into an effective z-axis dimension that would otherwise be difficult to achieve. Second, the method may enable manufacture of custom waveguides neural interface devices that are capable of region-specific illumination, while avoiding cost and yield problems that would otherwise occur. In other words, if the waveguide and neural device are integrated at the wafer-level, then the number of desirable/useful permutations of waveguide neural interface device design is so large that it impedes the profitability of the sale of such a device. The method can overcome this problem, transcending the practical limits of a wafer-level approach. Third, the method may separate yield issues in one aspect of either the neural device or waveguide fabrication, thereby improving average yield and lowering overall cost of the final combination waveguide neural interface product. However, in alternative embodiments, the method of making the waveguide neural interface device may include any suitable steps. For example, a portion or all of the neural device, waveguide, and circuit board components may be fabricated in an integrated fashion (e.g., fabricated in sequence with any photolithographic processes and/or any suitable technique, without the post-fabrication assembly described in method 300). For example, the neural device and the waveguide may be fabricated together in sequence as an integrated structure, and then coupled to the circuit board after fabrication.

Figure 16:
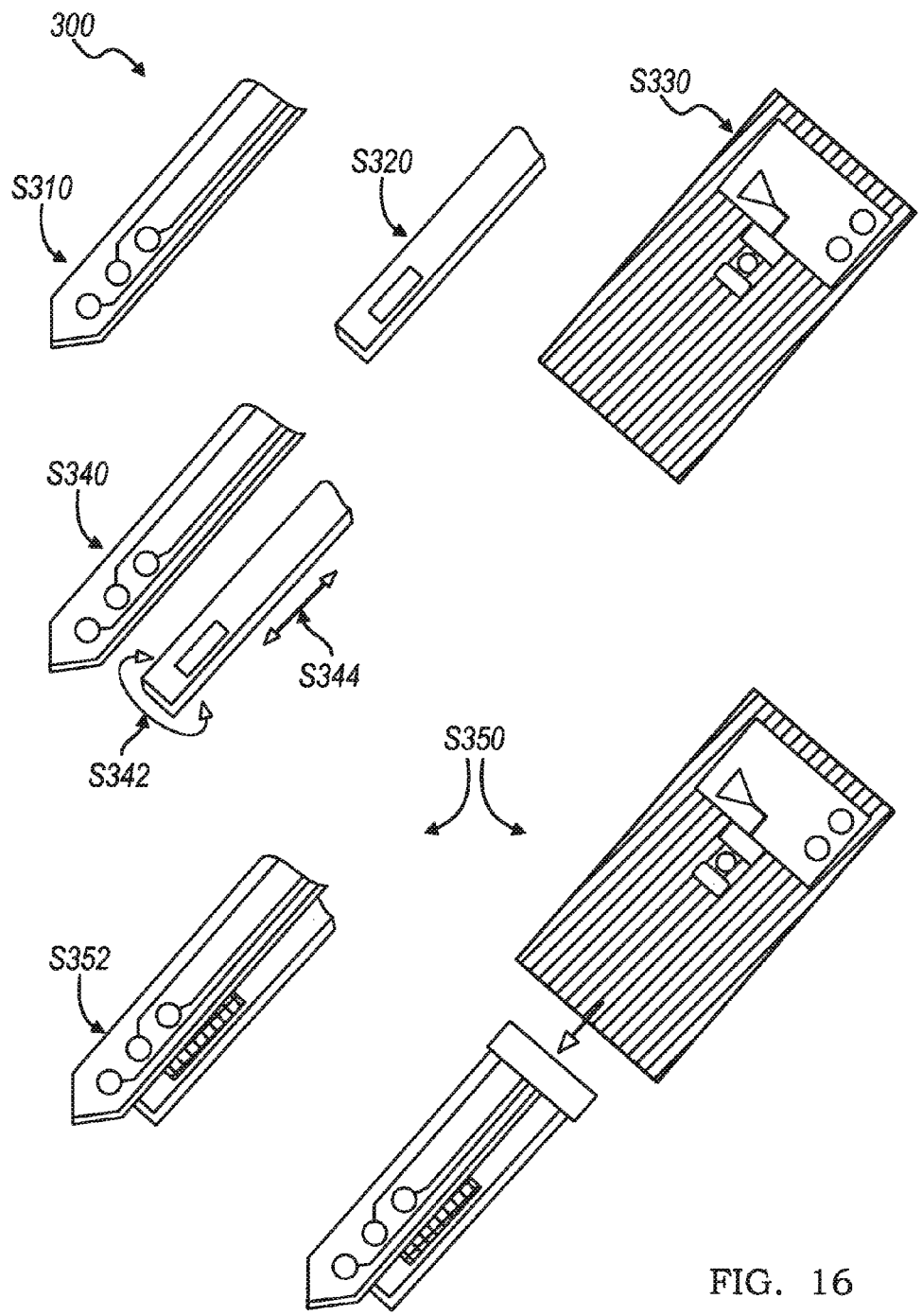
FIG. 16 is a schematic of the method of making a waveguide neural interface device of another preferred embodiment.

The steps of providing a neural device S310, providing a waveguide S320, and providing a circuit board S330 preferably include providing a neural device or neural probe, waveguide, and circuit board similar to those described above in the first preferred embodiment 100 and/or second preferred embodiment 200 of the waveguide neural interface device, but may alternatively include providing any suitable neural device, waveguide, and/or circuit board. Furthermore, although the method is primarily illustrated with a waveguide neural interface device of the first preferred embodiment, the method may be performed to assemble that of the second preferred embodiment (FIGS. 14 and 16) or any suitable waveguide neural interface device preferably having at least separate neural device and waveguide components, and perhaps additionally having a separate circuit board component.

Figure 15A:
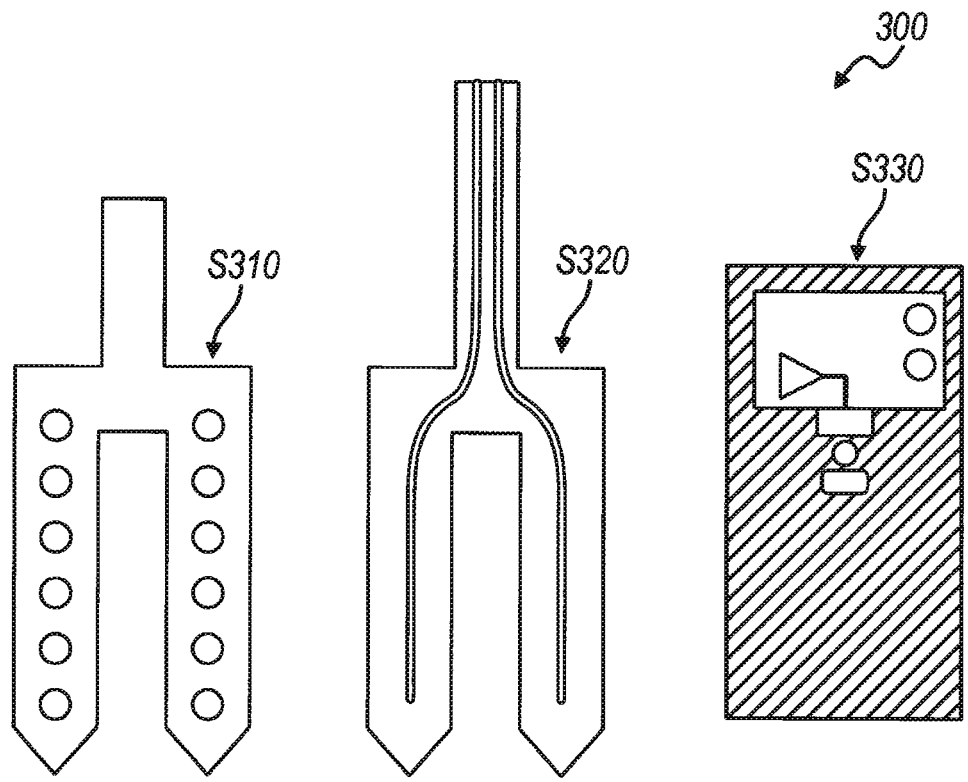
FIGS. 15A-15E are schematics of the method of making a waveguide neural interface device of a preferred embodiment.
Figure 15B:
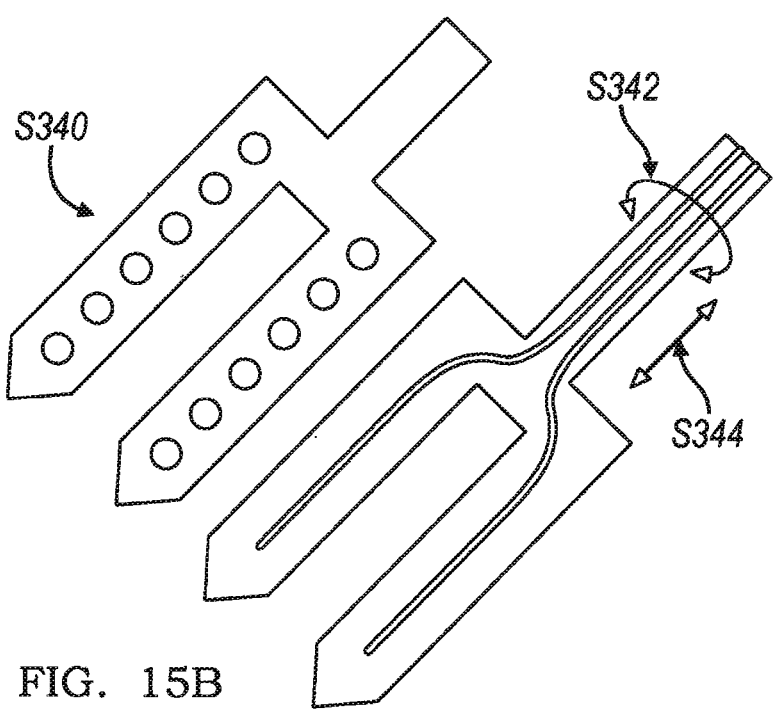

Step S340, which includes the step of orienting the light directing element of the waveguide to a predetermined angular orientation, functions to set the direction of redirected light to a particular direction. As shown in FIG. 15B, the step of orientating the light directing element preferably includes rotating the waveguide about the longitudinal axis of the waveguide to the predetermined angular orientation S342. However, the waveguide may be rotated about any suitable axis. Furthermore, the step of orienting the light directing element of the waveguide may include translating the waveguide along a longitudinal, lateral, or any suitable axis S344. Orienting the waveguide in this manner preferably enables another dimension of spatial variance along another axis, particularly features typically in an x-y plane to become features in the z-axis when rotated relative to the neural device. Step S340 enables further customization of the waveguide neural interface device.

Figure 15C:
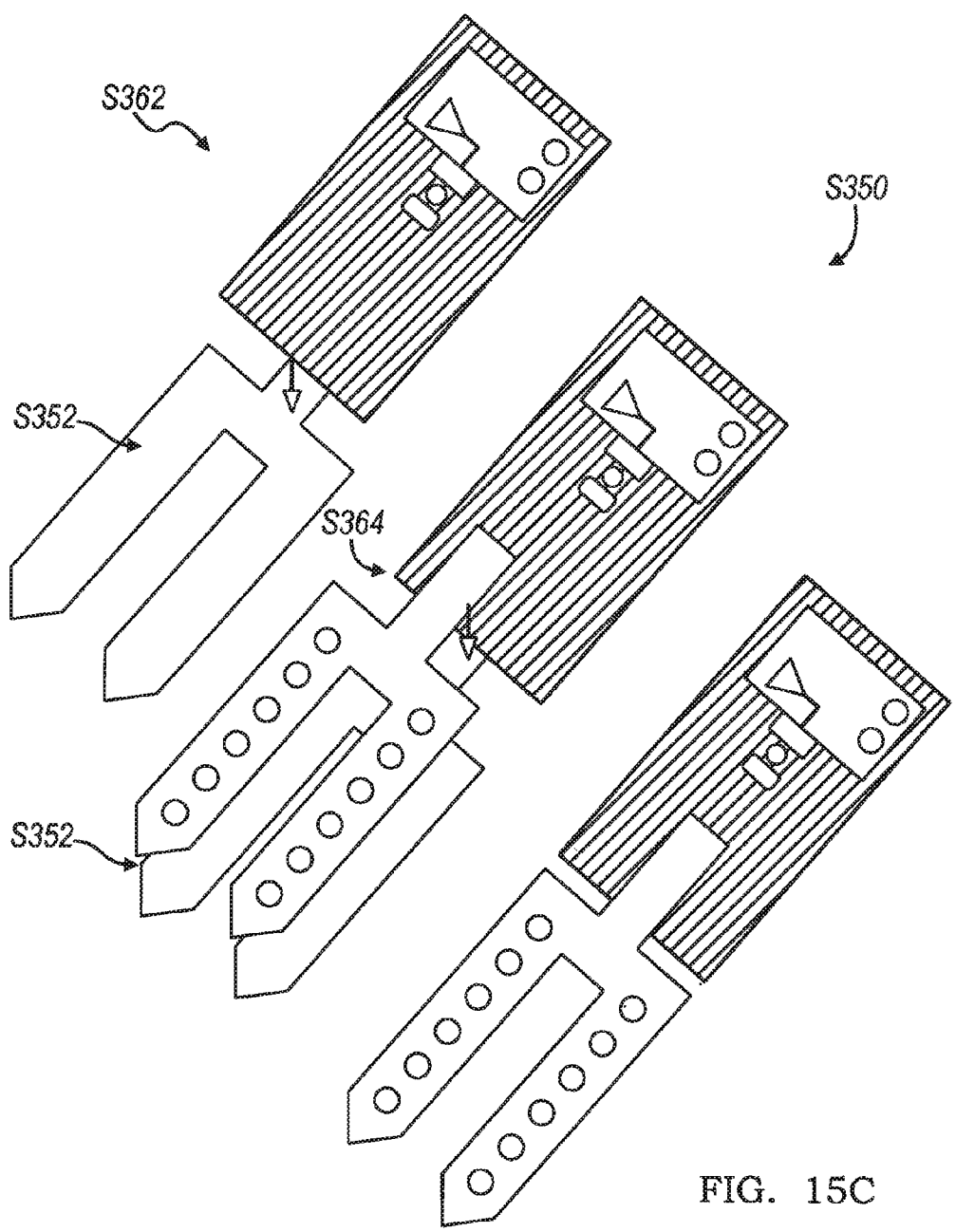
Figure 15D:
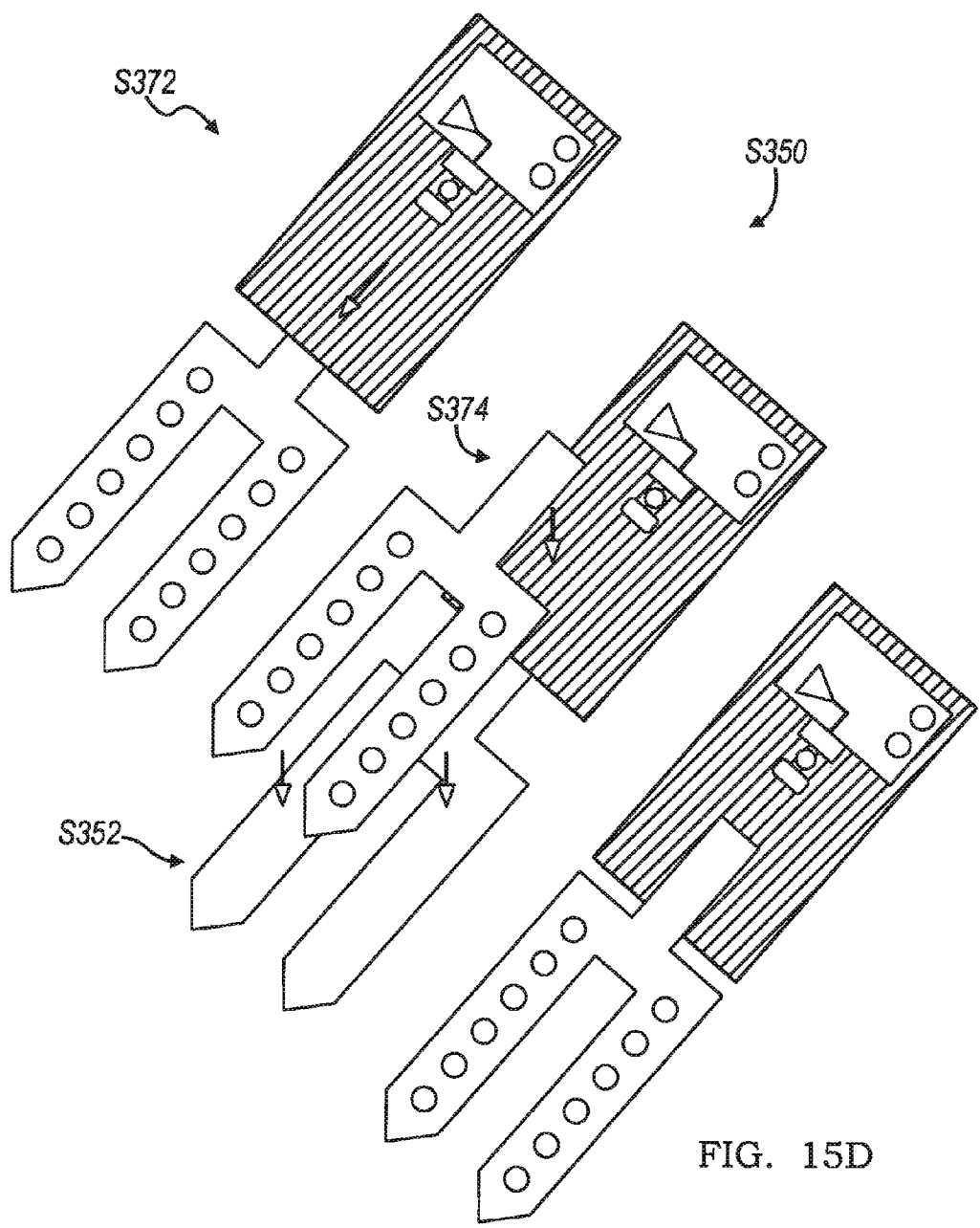
Figure 15E:
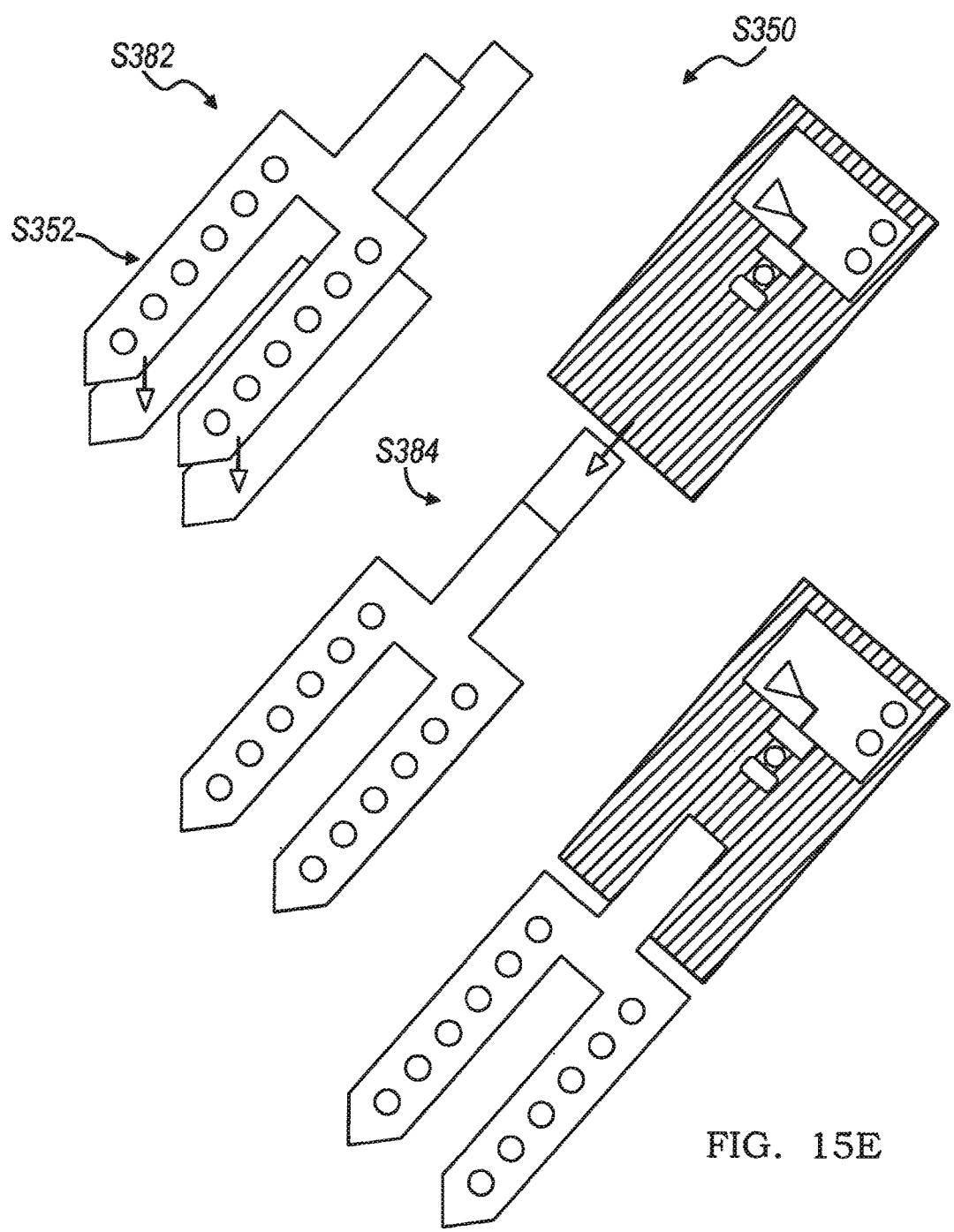

Step S350, which includes the step of coupling each structure of the group comprising the neural device, the waveguide, and the circuit board to at least one of the other structures in the group, functions to fix and assemble the structures of the group to form the waveguide neural interface device. Step S350 preferably includes fixing the waveguide at the predetermined angular orientation relative to the neural device and/or circuit board. In step S350, the three components (neural device, waveguide, and circuit board) may be mounted or attached in any order. In a first variation, as shown in FIG. 15C, step S350 includes coupling the waveguide and the circuit board to form a waveguide-circuit board structure S362 and coupling the neural probe and the waveguide-circuit board structure S364. In this variation, coupling the waveguide and the circuit board S350 may include coupling the waveguide to an optical face of the circuit board having optical components and coupling the neural device to an electrical face of the circuit board having electrical components. In a second variation, as shown in FIG. 15D, step S350 includes coupling the neural device and the circuit board to form a neural device-circuit board structure S372 and coupling the waveguide and the neural device-circuit board structure S374. In a third variation, as shown in FIG. 15E, step S350 includes coupling the waveguide and the neural device to form a waveguide-neural device structure S382 and coupling the circuit board and the waveguide-neural device structure S384. In summary of the variations of step S350, any order of assembly of the neural device, waveguide and circuit board may be used: (1) couple the waveguide and the circuit board, then couple the neural device and the waveguide-circuit board structure, (2) couple the neural device and the circuit board, then couple the waveguide and the neural device-circuit board structure; or (3) couple the waveguide and the neural device, then couple the circuit board and the waveguide-neural device structure. In any of these variations of step S350, coupling the circuit board to the waveguide may include coupling an optical coupler that transfers light from a light source to the waveguide. In any of these variations of step S350, coupling the circuit board to the neural device may include coupling an interconnect (e.g., a flexible interconnect) between the neural device and the circuit board to transfer electrical signals. The coupling step S350 may include layering or stacking two of the components (e.g. layering the neural device over the waveguide), wrapping one component (e.g., wrapping the neural device over the waveguide), connecting end to end (e.g., coupling the circuit board to an axial end of the neural device or waveguide), and/or any suitable coupling step. Furthermore, in other embodiments additional intermediary components may be introduced to indirectly couple any two of the structures. For example, both the neural device and the waveguide may be coupled to a common base such as a carrier, without the neural device and the waveguide being directly coupled to each other.

Step S350 of coupling may be performed manually and/or with machine assistance. One or more of the components may include features to aid component alignment, such as fiducial marks, tabs, and/or corresponding alignment holes. The steps of coupling any two of the structures may include applying an epoxy such a medical grade epoxy (e.g., Epoxy Tek H70E-2 or 320, which is designed to shield light) or a UV-curable epoxy, or using fasteners, or any suitable adhesive or other means for coupling. The steps of coupling any two of the structures may additionally and/or alternatively include applying a polymer overcoat around at least two of the structures in the group.

As a person skilled in the art will recognize from the previous detailed description and from the figures and claims, modifications and changes can be made to the preferred embodiments of the invention without departing from the scope of this invention defined in the following claims.

What is claimed is:

1. A method of assembling a waveguide neural interface device, comprising the steps of:

a) providing a substrate comprising a first proximal substrate branch and a second proximal substrate branch extending proximally from at least a distal substrate portion;

b) mounting at least one waveguide to the substrate, wherein the waveguide is configured to carry light along a light path from a proximal waveguide portion supported at the first proximal substrate branch to a distal waveguide portion including at least one distal light directing element supported at the distal substrate portion, the light directing element being configured to emit light carried by the waveguide away from a longitudinal axis of a distal portion of the light path;

c) supporting at least one electrode site on the distal substrate portion, wherein the at least one electrode site is electrically connected to an interconnect supported on the second proximal substrate branch;

d) providing a circuit board comprising a first circuit board face delineated from a second circuit board face by a fold line;

e) mounting the first and second proximal substrate branches supporting the respective proximal waveguide portion and the interconnect to the first circuit board face;

f) mounting a light source to the second circuit board face; and g) folding the circuit board along the fold line to thereby move the respective first and second circuit board faces into close proximity with each other so that the light source is positioned to shine light into the proximal waveguide portion at the first proximal substrate branch so that the shone light travels along the light path to then be emitted from the waveguide adjacent to the at least one electrode site by the light directing element at the distal substrate portion.

2. The method of claim 1, including orienting the light directing element by rotating the waveguide to a predetermined angular orientation with respect to the longitudinal axis of the distal portion of the light path.

3. The method of claim 1, including providing the circuit board comprising an electrical face as the first circuit board face and an optical face as the second circuit board face, wherein the optical face of the circuit board comprises optical components and the electrical face of the circuit board comprises at least one electrical component configured to interface with the at least one electrode site.

4. The method of claim 1, including fabricating the waveguide using a process selected from the group consisting of a micro-opto-electro-mechanical system (MOEMS), photolithography, microembossing, thermal nanoimprint lithography (NIL), and combined nanoimprinting and photolithography (CNP).

5. The method of claim 1, including fabricating the waveguide from a material selected from the group consisting of SU-8, poly (methyl methacrylate) (PMMA), perfluoropolymers, polydimethylsiloxane (PDMS), parylene, silicon dioxide ($SiO_2$), silicon nitride, silicon oxynitride, and silica.

6. The method of claim 1, including layering the waveguide over the substrate.

7. The method of claim 6, including wrapping the substrate around the waveguide.

8. A waveguide neural interface device, comprising;

a) a substrate comprising a first proximal substrate branch and a second proximal substrate branch extending proximally from at least a distal substrate portion;

b) at least one waveguide mounted to the substrate, wherein the waveguide is configured to carry light along a light path from a proximal waveguide portion supported at the first proximal substrate branch to a distal waveguide portion including at least one distal light directing element supported at the distal substrate portion, the light directing element being configured to emit light carried by the waveguide away from a longitudinal axis of a distal portion of the light path;

c) at least one electrode site supported by the distal substrate portion, wherein the at least one electrode site is electrically connected to an interconnect supported on the second proximal substrate branch;

d) a circuit board comprising a first circuit board face delineated from a second circuit board face by a fold line, wherein the first and second proximal substrate branches supporting the respective proximal waveguide portion and the interconnect are mounted to the first circuit board face; and e) a light source mounted to the second circuit board face, and f) wherein the circuit board is characterized as having been folded along the fold line so that the respective first and second circuit board faces are in close proximity with each other and with the light source positioned to shine light into the proximal waveguide portion at the first proximal substrate branch so that the shone light travels along the light path to then be emitted from the waveguide adjacent to the at least one electrode site by the light directing element at the distal substrate portion.

9. The waveguide neural interface device of claim 8, wherein there are at least two electrode sites, a first one being a recording electrode site that is configured to sample illuminated light and the other one being a stimulation electrode site that is configured to provide electrical stimulation to tissue.

10. The waveguide neural interface device of claim 9, wherein the light directing element is positioned to avoid direct illumination of the recording electrode site.

11. The waveguide neural interface device of claim 8, wherein the substrate has a shape selected from the group consisting of flat, concave, convex, and wavy.

12. The waveguide neural interface device of claim 8, wherein the light directing element is supported by the waveguide.

13. The waveguide neural interface device of claim 8, wherein the at least one waveguide has more than one light directing element.

14. The waveguide neural interface device of claim 8, wherein the substrate has either a cylindrical or an elliptical cross-section perpendicular to a length and wherein there are a plurality of electrode sites arranged axially along and circumferentially around the cylindrical- or elliptical-shaped substrate.

15. The waveguide neural interface device of claim 8, wherein the substrate is relatively flexible and the waveguide is relatively rigid.

16. The waveguide neural interface device of claim 8, wherein the waveguide has a tapered distal end configured for insertion into tissue.

17. The waveguide neural interface device of claim 8, wherein the waveguide comprises a cladding layer over an inner core, and wherein the cladding layer is configured to facilitate internal reflection of light along the inner core serving as the light path.

18. The waveguide neural interface device of claim 17, wherein the cladding layer is patterned to expose a portion of the inner core and wherein the light directing element comprises an exposed portion of the inner core.

19. The waveguide neural interface device of claim 8, wherein the light directing element comprises at least one light refractor.

20. The waveguide neural interface device of claim 8, wherein the light directing element comprises a reflector that is configured to reflect light in a proximal direction along the longitudinal axis of the distal portion of the light path.

21. The waveguide neural interface device of claim 8, wherein the light directing element comprises a lens configured to focus the emitted light to a variable focal point outside the waveguide.

22. The waveguide neural interface device of claim 21, wherein the lens is either a light crystal lens or a ferroelectric lens.

23. The waveguide neural interface device of claim 8, wherein the light directing element is a light scattering element selected from the group consisting of a Bragg reflector, surface corrugations, an optically dissipating coating, and optically dissipating molecules embedded in the waveguide.

24. The waveguide neural interface device of claim 8, wherein the light directing element comprises a filter that is configured to allow only a certain bandwidth of light to emit from the waveguide.

25. The waveguide neural interface device of claim 8, wherein the substrate comprises an aperture through which light emitting from the light directing element shines.

26. The waveguide neural interface device of claim 25, wherein the substrate comprises spaced apart front and back substrate faces and wherein the at least one electrode site is supported on one of the front and back substrate faces and the waveguide is supported on the other of the front and back substrate faces with the light emitting element configured to shine light through the aperture to illuminate tissue adjacent to the at least one electrode site.

27. The waveguide neural interface device of claim 8, wherein each of the first and second proximal substrate branches supports a respective waveguide.

28. The waveguide neural interface device of claim 27, wherein the distal substrate portion comprises first and second distal substrate branches, each distal substrate branch supporting at least one electrode site and a distal waveguide portion connected to at least one distal light directing element configured to emit light adjacent to the at least one electrode site.

29. The waveguide neural interface device of claim 8, wherein at least one of the first and second circuit board faces further support at least one electrical component and at least one optical component, and wherein:

a) the at least one electrical component is selected from the group consisting of a passive electrical component, an active electrical component, a bond pad for the at least one electrode site, a connector for interfacing to an external component, a current driver for a diode or LED, control electronics for providing a control signal, and a battery power source; and b) the at least one optical component is selected from the group consisting of a light collecting element, a light focusing element, and an optical filter.

30. The waveguide neural interface device of claim 29, wherein the distal substrate portion comprises first and second distal substrate branches, each distal substrate branch supporting at least one electrode site and a distal waveguide portion connected to at least one distal light directing element configured to emit light adjacent to the at least one electrode site.

31. The waveguide neural interface device of claim 8, wherein the light source is selected from the group consisting of a circuit board-mounted light-emitting diode (LED), a laser diode, a vertical cavity surface-emitting laser (VCSEL), an external laser, an external laser diode, and an external LED.

32. The waveguide neural interface device of claim 8, wherein the substrate is rotatable about an axis of the waveguide.

33. The waveguide neural interface device of claim 8, wherein the substrate is translatable along an axis of the waveguide.

34. A waveguide neural interface device, comprising:
  a) a substrate comprising a first proximal substrate branch and a second proximal substrate branch extending proximally from at least a distal substrate portion;
  b) at least one waveguide mounted to the substrate, wherein the waveguide comprises a cladding layer over an inner core with the cladding layer being configured to facilitate internal reflection of light along the inner core serving as a light path from a proximal waveguide portion supported at the first proximal substrate branch to a distal waveguide portion including at least one distal light directing element supported at the distal substrate portion, and wherein the cladding layer is patterned to expose a portion of the inner core with the exposed portion of the inner core serving as a light directing element configured to emit light shone along the inner core away from a longitudinal axis of a distal portion of the light path;
  c) at least one electrode site supported by the distal substrate portion, wherein the at least one electrode site is electrically connected to an interconnect supported on the second proximal substrate branch;
  d) a circuit board comprising a first circuit board face delineated from a second circuit board face by a fold line, wherein the first and second proximal substrate branches supporting the respective proximal waveguide portion and the interconnect are mounted to the first circuit board face; and
  e) a light source mounted to the second circuit board face, and
  f) wherein the circuit board is characterized as having been folded along the fold line so that the respective first and second circuit board faces are in close proximity with each other and with the light source positioned to shine light into the proximal waveguide portion at the first proximal substrate branch so that the shone light travels along the light path to then be emitted from the waveguide adjacent to the at least one electrode site by the light directing element at the distal substrate portion, and
  g) wherein the substrate is at least one of rotatable about an axis of the waveguide and translatable along the waveguide axis to thereby provide for selective adjustment of the emitted light with respect to the at least one electrode site.

* * * * *